(12) United States Patent
Ueda et al.

(10) Patent No.: US 7,294,491 B2
(45) Date of Patent: Nov. 13, 2007

(54) METHOD FOR PRODUCING L-GLUTAMIC ACID

(75) Inventors: Hiroshi Ueda, Kawasaki (JP); Kunihiko Toumori, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/265,288

(22) Filed: Nov. 3, 2005

(65) Prior Publication Data

US 2006/0084151 A1    Apr. 20, 2006

Related U.S. Application Data

(63) Continuation of application No. PCT/JP2004/006031, filed on May 7, 2004.

(30) Foreign Application Priority Data

May 7, 2003    (JP) .............................. 2003-128722

(51) Int. Cl.
  *C12P 13/14*    (2006.01)
  *C12N 1/12*     (2006.01)
  *C12N 1/36*     (2006.01)
  *C12N 1/20*     (2006.01)
(52) U.S. Cl. ................... 435/110; 435/252.1; 435/245; 435/252.3; 435/252.33
(58) Field of Classification Search ................ 435/110, 435/252.3, 847, 252.1, 252.33, 2
See application file for complete search history.

(56) References Cited

U.S. PATENT DOCUMENTS

| 3,032,474 | A |   | 5/1962 | Foster |
| 3,220,929 | A |   | 11/1965 | Kinoshita et al. |
| 5,908,768 | A |   | 6/1999 | Ono et al. |
| 6,197,559 | B1 | * | 3/2001 | Moriya et al. ............. 435/110 |
| 6,331,419 | B1 | * | 12/2001 | Moriya et al. ............. 435/110 |
| 6,596,517 | B2 | * | 7/2003 | Izui et al. .................. 435/110 |
| 6,653,110 | B2 | * | 11/2003 | Sato et al. ................. 435/110 |
| 6,881,861 | B2 |   | 4/2005 | Saitou et al. |
| 2001/0019836 | A1 |   | 9/2001 | Moriya et al. |
| 2002/0192772 | A1 |   | 12/2002 | Sato et al. |
| 2003/0003550 | A1 |   | 1/2003 | Nakamura et al. |
| 2003/0119153 | A1 |   | 6/2003 | Moriya et al. |
| 2005/0227334 | A1 |   | 10/2005 | Izui et al. |

FOREIGN PATENT DOCUMENTS

| EP | 0670370 | 9/1995 |
| EP | 0952221 | 10/1999 |
| EP | 0999282 | 5/2000 |
| EP | 1078989 | 2/2001 |
| EP | 1 233 070 | 8/2002 |
| EP | 1233068 | 8/2002 |
| EP | 1233069 | 8/2002 |
| EP | 1 233 068 | 11/2002 |
| EP | 1352966 | 10/2003 |
| JP | 36-017712 | 9/1961 |
| JP | 38-016459 | 8/1963 |
| JP | 45-011286 | 4/1970 |
| JP | 61-139398 | 6/1986 |
| JP | 61-268185 | 11/1986 |
| JP | 62-000288 | 1/1987 |
| JP | 63-214189 | 9/1988 |
| JP | 10-059911 | 3/1998 |
| WO | WO97/08294 | 3/1997 |

OTHER PUBLICATIONS

Hiramatsu S. Sudies on the polymorphic crystalization of L-glutamic acid in the presence of co-existant substances. Part II. Effects of amino acids and therir derivatives, peptides and proteins on the apha to beta polymorphic transition of L-glutamic acid crystal, Nippon Nogie Kagaku Kaishi (19977), 51(1), 38-46; abstract.*

Kitamura M. et al., In situ Observation of Growth Process of alpha-L-Glutamic Acid with Atomic Force Microscopy, Journal of Colloid and Interface Science, 2000, 224, 311-316.*

International Search Report for PCT App. No. PCT/JP2004/006031 (Jun. 22, 2004).

Bernal, J. D., "Kürzere Originalmitteilunge und Notizen. The Crystal Structure of the Natural Amino Acids and Related Compounds," Z. Krist. 1931;78:363-369.

Hirokawa, S., "A New Modification of L-Glutamic Acid and its Crystal Structure," Acta Cryst. 1955;8:637-641.

Takahashi, H., et al., "Quantitative Analysis of Mixtures of L-Glutamic Acid Polymorphs by X-Ray Diffraction," Bull. Chem. Soc. Japan 1962;35:923-926.

International Preliminary Report on Patentability for PCT Appl. No. PCT/JP2004/006031 (Mar. 23, 2006).

Bailey, J. E., "Toward a Science of Metabolic Engineering," Science 1991;252:1668-1675.

Borichewski, R. M., "Keto Acids as Growth-limiting Factors in Autotrophic Growth of *Thiobacillus thiooxidans*," J. Bacteriol. 1967;93(2):597-599.

(Continued)

*Primary Examiner*—Rebecca E. Prouty
*Assistant Examiner*—Malgorzata A. Walicka
(74) *Attorney, Agent, or Firm*—Cermak Kenealy & Vaidya LLP; Shelly Guest Cermak

(57) ABSTRACT

The present invention provides a method for producing L-glutamic acid by fermentation, by culturing in a liquid medium a microorganism that can metabolize a carbon source at a specific pH, and wherein said medium contains a carbon source and L-glutamic acid at a saturation concentration, and wherein said microorganism is able to cause accumulation of an amount of L-glutamic acid in a liquid medium having said pH, wherein said amount exceeds the amount of L-glutamic acid at said saturation concentration when the pH of the medium is controlled so that L-glutamic acid is precipitated, making L-lysine exist in the medium when L-glutaminc acid concentration is lower than the concentration at which natural crystallization of L-glutamic acid occurs, and precipitating the α-form crystals of L-glutamic acid.

6 Claims, 7 Drawing Sheets

OTHER PUBLICATIONS

Chao, K.-C., et al., "A Glutamic Acid-Producing Bacillus," J. Bacteriol 1959;77(6):715-725.

Jetten, M.S., et al., "Recent advances in the physiologu and genetics of amino acod-producing bacteria," Crit. Rev. Biotechnol. 1995;15(1):73-103 (abstract).

Kwon, S.-W., et al., "Phylogenetic Analysis of *Erwinia* Species Based on 16S rRNA Gene Sequences," Int. J. Sys. Bacteriol. 1997;47(4):1061-1067.

Mergaert, J., et al., "Transfer of *Erwinia ananas* (synonym, *Erwinia uredovora*) and *Erwinia stewartii* to the Genus *Pantoea* emend. as *Pantoea ananas* (Serrano 1928) comb. nov. and *Pantoea stewartii* (Smith 1898) comb. nov., Respectively, and Description of *Pantoea stewartii* subsp. *indologenes* subsp. nov." Int. J. Sys. Bacteriol. 1993;43(1):162-173.

WPI/Derwent Abstract, "Manufacturing L-glutamic acid by fermentation for foodstuff, pharmaceutical—comprises culturing *Corynebacterium striatam* in culture medium," JP-11009296 (1999) (abstract).

U.S. Appl. No. 09/419,611, filed Oct. 18, 1999, inventor Izui et al., now US Patent 7,247,459.

* cited by examiner

SEQUENCE LISTING

```
<160> NUMBER OF SEQ ID NOS: 13

<210> SEQ ID NO 1
<211> LENGTH: 4556
<212> TYPE: DNA
<213> ORGANISM: Pantoea ananatis
<220> FEATURE:
<221> NAME/KEY: CDS
<222> LOCATION: (2)..(121)
<220> FEATURE:
<221> NAME/KEY: CDS
<222> LOCATION: (322)..(3129)
<220> FEATURE:
<221> NAME/KEY: CDS
<222> LOCATION: (3145)..(4368)
<220> FEATURE:
<221> NAME/KEY: CDS
<222> LOCATION: (4437)..(4556)

<400> SEQUENCE: 1
```

| | | | | | | | | | | | | | | | |
|---|---|---|---|---|---|---|---|---|---|---|---|---|---|---|---|
| t | gca | ttc | agc | gtt | ttc | cgc | tgt | cac | agc | atc | atg | aac | tgt | gta agt gtt | 49 |
|   | Ala | Phe | Ser | Val | Phe | Arg | Cys | His | Ser | Ile | Met | Asn | Cys | Val Ser Val |   |
|   | 1   |     |     | 5   |     |     |     |     | 10  |     |     |     |     | 15          |   |

| tgt | cct | aaa | ggg | cta | aac | ccg | acg | cgc | gct | atc | ggc | cac | att | aag | tcg | 97 |
|---|---|---|---|---|---|---|---|---|---|---|---|---|---|---|---|---|
| Cys | Pro | Lys | Gly | Leu | Asn | Pro | Thr | Arg | Ala | Ile | Gly | His | Ile | Lys | Ser | |
| | | | 20 | | | | | 25 | | | | | 30 | | | |

| atg | ctg | ctg | caa | cgc | agc | gcg | tagttatacc accgggaacc tcaggttccc | 148 |
|---|---|---|---|---|---|---|---|---|
| Met | Leu | Leu | Gln | Arg | Ser | Ala | | |
| | | | 35 | | | | | |

| ggtattttac ggaagcctct gtaaacgcgg tcccaaccac gtttacaaag gttcccttac | 208 |
|---|---|
| gggccgggcg cgcgctgcgc acagtgctcg tatcgctgaa ctcactacgg caaaccgcga | 268 |
| aagcggcaac aaatgaaacc tcaaaaaagc ataacattgc ttaagggatc aca atg | 324 |
| | Met |
| | 1 |

| cag | aac | agc | gcg | atg | aag | ccc | tgg | ctg | gac | tcc | tcc | tgg | ctg | gcc | ggc | 372 |
|---|---|---|---|---|---|---|---|---|---|---|---|---|---|---|---|---|
| Gln | Asn | Ser | Ala | Met | Lys | Pro | Trp | Leu | Asp | Ser | Ser | Trp | Leu | Ala | Gly | |
| | | | 5 | | | | | 10 | | | | | 15 | | | |

| gcg | aat | cag | tct | tac | ata | gag | caa | ctc | tat | gag | gat | ttc | ctg | acc | gat | 420 |
|---|---|---|---|---|---|---|---|---|---|---|---|---|---|---|---|---|
| Ala | Asn | Gln | Ser | Tyr | Ile | Glu | Gln | Leu | Tyr | Glu | Asp | Phe | Leu | Thr | Asp | |
| | | 20 | | | | | 25 | | | | | 30 | | | | |

| cct | gac | tct | gtg | gat | gca | gtg | tgg | cgc | tcg | atg | ttc | caa | cag | tta | cca | 468 |
|---|---|---|---|---|---|---|---|---|---|---|---|---|---|---|---|---|
| Pro | Asp | Ser | Val | Asp | Ala | Val | Trp | Arg | Ser | Met | Phe | Gln | Gln | Leu | Pro | |
| | 35 | | | | 40 | | | | | 45 | | | | | | |

| ggc | acg | gga | gtg | aaa | cct | gag | cag | ttc | cac | tcc | gca | act | cgc | gaa | tat | 516 |
|---|---|---|---|---|---|---|---|---|---|---|---|---|---|---|---|---|
| Gly | Thr | Gly | Val | Lys | Pro | Glu | Gln | Phe | His | Ser | Ala | Thr | Arg | Glu | Tyr | |
| 50 | | | | | 55 | | | | | 60 | | | | | 65 | |

| ttc | cgt | cgc | ctg | gcg | aaa | gac | gca | tct | cgt | tac | acc | tcc | tca | gtt | acc | 564 |
|---|---|---|---|---|---|---|---|---|---|---|---|---|---|---|---|---|
| Phe | Arg | Arg | Leu | Ala | Lys | Asp | Ala | Ser | Arg | Tyr | Thr | Ser | Ser | Val | Thr | |
| | | | 70 | | | | | 75 | | | | | 80 | | | |

| gat | ccg | gca | acc | aac | tcc | aaa | caa | gtg | aaa | gtg | ctg | cag | ctg | att | aac | 612 |
|---|---|---|---|---|---|---|---|---|---|---|---|---|---|---|---|---|
| Asp | Pro | Ala | Thr | Asn | Ser | Lys | Gln | Val | Lys | Val | Leu | Gln | Leu | Ile | Asn | |
| | | | 85 | | | | | 90 | | | | | 95 | | | |

| gcg | ttt | cgt | ttc | cgc | gga | cat | cag | gaa | gca | aat | ctc | gat | ccg | ctt | ggc | 660 |
|---|---|---|---|---|---|---|---|---|---|---|---|---|---|---|---|---|
| Ala | Phe | Arg | Phe | Arg | Gly | His | Gln | Glu | Ala | Asn | Leu | Asp | Pro | Leu | Gly | |
| | | 100 | | | | | 105 | | | | | 110 | | | | |

| ctg | tgg | aaa | cag | gac | cgc | gtt | gcc | gat | ctc | gat | cct | gcc | ttt | cac | gat | 708 |
|---|---|---|---|---|---|---|---|---|---|---|---|---|---|---|---|---|
| Leu | Trp | Lys | Gln | Asp | Arg | Val | Ala | Asp | Leu | Asp | Pro | Ala | Phe | His | Asp | |
| | 115 | | | | 120 | | | | | 125 | | | | | | |

| ctg | acc | gac | gcc | gat | ttt | cag | gaa | agc | ttt | aac | gta | ggt | tct | ttt | gcc | 756 |
|---|---|---|---|---|---|---|---|---|---|---|---|---|---|---|---|---|
| Leu | Thr | Asp | Ala | Asp | Phe | Gln | Glu | Ser | Phe | Asn | Val | Gly | Ser | Phe | Ala | |
| 130 | | | | | 135 | | | | | 140 | | | | | 145 | |

| | |
|---|---|
| att ggc aaa gaa acc atg aag ctg gcc gat ctg ttc gac gcg ctg aag<br>Ile Gly Lys Glu Thr Met Lys Leu Ala Asp Leu Phe Asp Ala Leu Lys<br>             150                 155               160 | 804 |
| cag acc tac tgt ggc tcg att ggt gca gag tat atg cac atc aat aac<br>Gln Thr Tyr Cys Gly Ser Ile Gly Ala Glu Tyr Met His Ile Asn Asn<br>             165                 170               175 | 852 |
| acc gaa gag aaa cgc tgg atc cag cag cgt atc gaa tcc ggt gcg agc<br>Thr Glu Glu Lys Arg Trp Ile Gln Gln Arg Ile Glu Ser Gly Ala Ser<br>180                 185                 190 | 900 |
| cag acg tca ttc agt ggc gaa gag aaa aaa ggt ttc ctg aaa gag ctg<br>Gln Thr Ser Phe Ser Gly Glu Glu Lys Lys Gly Phe Leu Lys Glu Leu<br>        195                 200               205 | 948 |
| acc gcg gca gaa ggg ctg gaa aaa tat ctg ggc gcg aaa ttc ccg ggt<br>Thr Ala Ala Glu Gly Leu Glu Lys Tyr Leu Gly Ala Lys Phe Pro Gly<br>210                 215                 220               225 | 996 |
| gca aaa cgt ttc tcg ctg gaa ggc ggt gat gcg ctg gtg ccg atg ctg<br>Ala Lys Arg Phe Ser Leu Glu Gly Gly Asp Ala Leu Val Pro Met Leu<br>             230                 235               240 | 1044 |
| cgc gag atg att cgt cat gcg ggc aaa agc ggc aca cgt gaa gtg gta<br>Arg Glu Met Ile Arg His Ala Gly Lys Ser Gly Thr Arg Glu Val Val<br>             245                 250               255 | 1092 |
| ctg ggg atg gcg cac cgt ggc cgt ctt aac gta ctg att aac gta ctg<br>Leu Gly Met Ala His Arg Gly Arg Leu Asn Val Leu Ile Asn Val Leu<br>             260                 265               270 | 1140 |
| ggt aaa aag cca cag gat ctg ttc gac gaa ttc tcc ggt aaa cac aaa<br>Gly Lys Lys Pro Gln Asp Leu Phe Asp Glu Phe Ser Gly Lys His Lys<br>275                 280                 285 | 1188 |
| gag cat ctg ggc acc ggt gat gtg aag tat cac atg ggc ttc tct tcg<br>Glu His Leu Gly Thr Gly Asp Val Lys Tyr His Met Gly Phe Ser Ser<br>290                 295                 300               305 | 1236 |
| gat att gaa acc gaa ggt ggt ctg gtg cat ctg gcg ctg gcg ttt aac<br>Asp Ile Glu Thr Glu Gly Gly Leu Val His Leu Ala Leu Ala Phe Asn<br>             310                 315               320 | 1284 |
| ccg tct cac ctg gaa att gtc agc ccg gtg gtc atg gga tcg gta cgt<br>Pro Ser His Leu Glu Ile Val Ser Pro Val Val Met Gly Ser Val Arg<br>        325                 330               335 | 1332 |
| gca cgt ctc gat cgt ctg gcc gaa ccg gtc agc aat aaa gtg ttg cct<br>Ala Arg Leu Asp Arg Leu Ala Glu Pro Val Ser Asn Lys Val Leu Pro<br>340                 345                 350 | 1380 |
| atc acc att cac ggt gat gcg gcg gtg att ggt cag ggc gtg gtt cag<br>Ile Thr Ile His Gly Asp Ala Ala Val Ile Gly Gln Gly Val Val Gln<br>        355                 360               365 | 1428 |
| gaa acc ctg aac atg tct cag gcg cgc ggc tac gaa gtg ggc ggc acg<br>Glu Thr Leu Asn Met Ser Gln Ala Arg Gly Tyr Glu Val Gly Gly Thr<br>370                 375                 380               385 | 1476 |
| gta cgt atc gtc att aac aac cag gtt ggt ttt acc acc tcc aac ccg<br>Val Arg Ile Val Ile Asn Asn Gln Val Gly Phe Thr Thr Ser Asn Pro<br>             390                 395               400 | 1524 |
| aaa gat gcg cgt tca acc ccg tac tgt act gac atc ggc aag atg gtg<br>Lys Asp Ala Arg Ser Thr Pro Tyr Cys Thr Asp Ile Gly Lys Met Val<br>        405                 410               415 | 1572 |
| ctg gca ccg att ttc cac gtc aat gct gac gat ccg gaa gcg gtg gcc<br>Leu Ala Pro Ile Phe His Val Asn Ala Asp Asp Pro Glu Ala Val Ala<br>420                 425                 430 | 1620 |
| ttt gtt acc cgc ctg gcg ctg gac tat cgc aac acc ttc aaa cgc gat<br>Phe Val Thr Arg Leu Ala Leu Asp Tyr Arg Asn Thr Phe Lys Arg Asp<br>        435                 440               445 | 1668 |
| gtg ttt atc gat ctg gtg tgc tat cgc cgt cat ggt cac aac gag gcg<br>Val Phe Ile Asp Leu Val Cys Tyr Arg Arg His Gly His Asn Glu Ala | 1716 |

-continued

```
                450                 455                 460                 465
gat gag cca agt gct acc cag ccg ttg atg tac cag aaa atc aaa aag       1764
Asp Glu Pro Ser Ala Thr Gln Pro Leu Met Tyr Gln Lys Ile Lys Lys
                        470                 475                 480 cat ccg acg ccg cgt aaa att tac gcc gat cgt ctg gaa ggc gaa ggt       1812
His Pro Thr Pro Arg Lys Ile Tyr Ala Asp Arg Leu Glu Gly Glu Gly
                485                 490                 495 gtc gcg tcg cag gaa gat gcc acc gag atg gtg aac ctg tac cgc gat       1860
Val Ala Ser Gln Glu Asp Ala Thr Glu Met Val Asn Leu Tyr Arg Asp
            500                 505                 510 gcg ctc gat gcg ggc gaa tgc gtg gtg ccg gaa tgg cgt ccg atg agc       1908
Ala Leu Asp Ala Gly Glu Cys Val Val Pro Glu Trp Arg Pro Met Ser
        515                 520                 525 ctg cac tcc ttc acg tgg tcg cct tat ctg aac cac gaa tgg gat gag       1956
Leu His Ser Phe Thr Trp Ser Pro Tyr Leu Asn His Glu Trp Asp Glu
530                 535                 540                 545 cct tat ccg gca cag gtt gac atg aaa cgc ctg aag gaa ctg gca ttg       2004
Pro Tyr Pro Ala Gln Val Asp Met Lys Arg Leu Lys Glu Leu Ala Leu
                    550                 555                 560 cgt atc agc cag gtc cct gag cag att gaa gtg cag tcg cgc gtg gcc       2052
Arg Ile Ser Gln Val Pro Glu Gln Ile Glu Val Gln Ser Arg Val Ala
                565                 570                 575 aag atc tat aac gat cgc aag ctg atg gcc gaa ggc gag aaa gcg ttc       2100
Lys Ile Tyr Asn Asp Arg Lys Leu Met Ala Glu Gly Glu Lys Ala Phe
            580                 585                 590 gac tgg ggc ggt gcc gag aat ctg gcg tac gcc acg ctg gtg gat gaa       2148
Asp Trp Gly Gly Ala Glu Asn Leu Ala Tyr Ala Thr Leu Val Asp Glu
        595                 600                 605 ggt att ccg gtt cgc ctc tcg ggt gaa gac tcc ggt cgt gga acc ttc       2196
Gly Ile Pro Val Arg Leu Ser Gly Glu Asp Ser Gly Arg Gly Thr Phe
610                 615                 620                 625 ttc cat cgc cac gcg gtc gtg cac aac cag gct aac ggt tca acc tat       2244
Phe His Arg His Ala Val Val His Asn Gln Ala Asn Gly Ser Thr Tyr
                    630                 635                 640 acg ccg ctg cac cat att cat aac agc cag ggc gag ttc aaa gtc tgg       2292
Thr Pro Leu His His Ile His Asn Ser Gln Gly Glu Phe Lys Val Trp
                645                 650                 655 gat tcg gtg ctg tct gaa gaa gcg gtg ctg gcg ttt gaa tac ggt tac       2340
Asp Ser Val Leu Ser Glu Glu Ala Val Leu Ala Phe Glu Tyr Gly Tyr
            660                 665                 670 gcc acg gct gag ccg cgc gtg ctg acc atc tgg gaa gcg cag ttt ggt       2388
Ala Thr Ala Glu Pro Arg Val Leu Thr Ile Trp Glu Ala Gln Phe Gly
        675                 680                 685 gac ttt gcc aac ggt gct cag gtg gtg att gac cag ttc atc agc tct       2436
Asp Phe Ala Asn Gly Ala Gln Val Val Ile Asp Gln Phe Ile Ser Ser
690                 695                 700                 705 ggc gaa cag aag tgg ggc cgt atg tgt ggc ctg gtg atg ttg ctg ccg       2484
Gly Glu Gln Lys Trp Gly Arg Met Cys Gly Leu Val Met Leu Leu Pro
                    710                 715                 720 cat ggc tac gaa ggt cag gga ccg gaa cac tcc tct gcc cgt ctg gaa       2532
His Gly Tyr Glu Gly Gln Gly Pro Glu His Ser Ser Ala Arg Leu Glu
                725                 730                 735 cgc tat ctg caa ctt tgc gcc gag cag aac atg cag gtt tgc gtc ccg       2580
Arg Tyr Leu Gln Leu Cys Ala Glu Gln Asn Met Gln Val Cys Val Pro
            740                 745                 750 tcg acg ccg gct cag gtg tat cac atg ctg cgc cgt cag gcg ctg cgc       2628
Ser Thr Pro Ala Gln Val Tyr His Met Leu Arg Arg Gln Ala Leu Arg
        755                 760                 765 ggg atg cgc cgt ccg ctg gtg gtg atg tcg ccg aag tcg ctg tta cgc       2676
```

```
Gly Met Arg Arg Pro Leu Val Val Met Ser Pro Lys Ser Leu Leu Arg
770                 775                 780                 785 cat cca ctg gcg atc tcg tcg ctg gat gaa ctg gca aac ggc agt ttc    2724
His Pro Leu Ala Ile Ser Ser Leu Asp Glu Leu Ala Asn Gly Ser Phe
                    790                 795                 800 cag ccg gcc att ggt gag atc gac gat ctg gat ccg cag ggc gtg aaa    2772
Gln Pro Ala Ile Gly Glu Ile Asp Asp Leu Asp Pro Gln Gly Val Lys
                805                 810                 815 cgc gtc gtg ctg tgc tcc ggt aag gtt tac tac gat ctg ctg gaa cag    2820
Arg Val Val Leu Cys Ser Gly Lys Val Tyr Tyr Asp Leu Leu Glu Gln
                820                 825                 830 cgt cgt aaa gac gag aaa acc gat gtt gcc atc gtg cgc atc gaa cag    2868
Arg Arg Lys Asp Glu Lys Thr Asp Val Ala Ile Val Arg Ile Glu Gln
            835                 840                 845 ctt tac ccg ttc ccg cat cag gcg gta cag gaa gca ttg aaa gcc tat    2916
Leu Tyr Pro Phe Pro His Gln Ala Val Gln Glu Ala Leu Lys Ala Tyr
850                 855                 860                 865 tct cac gta cag gac ttt gtc tgg tgc cag gaa gag cct ctg aac cag    2964
Ser His Val Gln Asp Phe Val Trp Cys Gln Glu Glu Pro Leu Asn Gln
                870                 875                 880 ggc gcc tgg tac tgt agc cag cat cat ttc cgt gat gtc gtg ccg ttt    3012
Gly Ala Trp Tyr Cys Ser Gln His His Phe Arg Asp Val Val Pro Phe
                885                 890                 895 ggt gcc acc ctg cgt tat gca ggt cgc ccg gca tcg gct tct ccg gcc    3060
Gly Ala Thr Leu Arg Tyr Ala Gly Arg Pro Ala Ser Ala Ser Pro Ala
                900                 905                 910 gtg ggt tat atg tcc gta cac caa caa cag cag caa gac ctg gtt aat    3108
Val Gly Tyr Met Ser Val His Gln Gln Gln Gln Gln Asp Leu Val Asn
        915                 920                 925 gac gca ctg aac gtc aat taattaaaag gaaagata atg agt agc gta gat    3159
Asp Ala Leu Asn Val Asn                         Met Ser Ser Val Asp
930                 935                           1                 5 att ctc gtt ccc gac ctg cct gaa tcg gtt gca gat gcc aca gta gca    3207
Ile Leu Val Pro Asp Leu Pro Glu Ser Val Ala Asp Ala Thr Val Ala
                10                  15                  20 acc tgg cac aag aaa cca ggc gat gca gtc agc cgc gat gaa gtc atc    3255
Thr Trp His Lys Lys Pro Gly Asp Ala Val Ser Arg Asp Glu Val Ile
            25                  30                  35 gtc gaa att gaa act gac aaa gtc gtg ctg gaa gtg ccg gca tct gcc    3303
Val Glu Ile Glu Thr Asp Lys Val Val Leu Glu Val Pro Ala Ser Ala
            40                  45                  50 gat ggc gtg ctg gaa gcc gtg ctg gaa gac gaa ggg gca acc gtt acg    3351
Asp Gly Val Leu Glu Ala Val Leu Glu Asp Glu Gly Ala Thr Val Thr
55                  60                  65 tcc cgc cag atc ctg ggt cgc ctg aaa gaa ggc aac agt gcg ggt aaa    3399
Ser Arg Gln Ile Leu Gly Arg Leu Lys Glu Gly Asn Ser Ala Gly Lys
70                  75                  80                  85 gaa agc agt gcc aaa gcg gaa agc aat gac acc acg cca gcc cag cgt    3447
Glu Ser Ser Ala Lys Ala Glu Ser Asn Asp Thr Thr Pro Ala Gln Arg
                90                  95                  100 cag aca gcg tcg ctt gaa gaa gag agc agc gat gcg ctc agc ccg gcg    3495
Gln Thr Ala Ser Leu Glu Glu Glu Ser Ser Asp Ala Leu Ser Pro Ala
            105                 110                 115 atc cgt cgc ctg att gcg gag cat aat ctt gac gct gcg cag atc aaa    3543
Ile Arg Arg Leu Ile Ala Glu His Asn Leu Asp Ala Ala Gln Ile Lys
            120                 125                 130 ggc acc ggc gta ggc gga cgt tta acg cgt gaa gac gtt gaa aaa cat    3591
Gly Thr Gly Val Gly Gly Arg Leu Thr Arg Glu Asp Val Glu Lys His
135                 140                 145
```

```
ctg gcg aac aaa ccg cag gct gag aaa gcc gcc gcg cca gcg gcg ggt    3639
Leu Ala Asn Lys Pro Gln Ala Glu Lys Ala Ala Ala Pro Ala Ala Gly
150                 155                 160                 165 gca gca acg gct cag cag cct gtt gcc aac cgc agc gaa aaa cgt gtt    3687
Ala Ala Thr Ala Gln Gln Pro Val Ala Asn Arg Ser Glu Lys Arg Val
                170                 175                 180 ccg atg acg cgt tta cgt aag cgc gtc gcg gag cgt ctg ctg gaa gcc    3735
Pro Met Thr Arg Leu Arg Lys Arg Val Ala Glu Arg Leu Leu Glu Ala
            185                 190                 195 aag aac agc acc gcc atg ttg acg acc ttc aac gaa atc aac atg aag    3783
Lys Asn Ser Thr Ala Met Leu Thr Thr Phe Asn Glu Ile Asn Met Lys
        200                 205                 210 ccg att atg gat ctg cgt aag cag tac ggc gat gcg ttc gag aag cgt    3831
Pro Ile Met Asp Leu Arg Lys Gln Tyr Gly Asp Ala Phe Glu Lys Arg
    215                 220                 225 cac ggt gtg cgt ctg ggc ttt atg tct ttc tac atc aag gcc gtg gtc    3879
His Gly Val Arg Leu Gly Phe Met Ser Phe Tyr Ile Lys Ala Val Val
230                 235                 240                 245 gaa gcg ctg aag cgt tat cca gaa gtc aac gcc tct atc gat ggc gaa    3927
Glu Ala Leu Lys Arg Tyr Pro Glu Val Asn Ala Ser Ile Asp Gly Glu
                250                 255                 260 gac gtg gtg tac cac aac tat ttc gat gtg agt att gcc gtc tct acg    3975
Asp Val Val Tyr His Asn Tyr Phe Asp Val Ser Ile Ala Val Ser Thr
            265                 270                 275 cca cgc gga ctg gtg acg cct gtc ctg cgt gac gtt gat gcg ctg agc    4023
Pro Arg Gly Leu Val Thr Pro Val Leu Arg Asp Val Asp Ala Leu Ser
        280                 285                 290 atg gct gac atc gag aag aaa att aaa gaa ctg gca gtg aaa ggc cgt    4071
Met Ala Asp Ile Glu Lys Lys Ile Lys Glu Leu Ala Val Lys Gly Arg
    295                 300                 305 gac ggc aag ctg acg gtt gac gat ctg acg ggc ggt aac ttt acc atc    4119
Asp Gly Lys Leu Thr Val Asp Asp Leu Thr Gly Gly Asn Phe Thr Ile
310                 315                 320                 325 acc aac ggt ggt gtg ttc ggt tcg ctg atg tct acg cca atc atc aac    4167
Thr Asn Gly Gly Val Phe Gly Ser Leu Met Ser Thr Pro Ile Ile Asn
                330                 335                 340 ccg cca cag agc gcg att ctg ggc atg cac gcc att aaa gat cgt cct    4215
Pro Pro Gln Ser Ala Ile Leu Gly Met His Ala Ile Lys Asp Arg Pro
            345                 350                 355 atg gcg gtc aat ggt cag gtt gtg atc ctg cca atg atg tac ctg gct    4263
Met Ala Val Asn Gly Gln Val Val Ile Leu Pro Met Met Tyr Leu Ala
        360                 365                 370 ctc tcc tac gat cac cgt tta atc gat ggt cgt gaa tct gtc ggc tat    4311
Leu Ser Tyr Asp His Arg Leu Ile Asp Gly Arg Glu Ser Val Gly Tyr
375                 380                 385 ctg gtc gcg gtg aaa gag atg ctg gaa gat ccg gcg cgt ctg ctg ctg    4359
Leu Val Ala Val Lys Glu Met Leu Glu Asp Pro Ala Arg Leu Leu Leu
390                 395                 400                 405 gat gtc tgattcatca ctgggcacgc gttgcgtgcc aatctcaat actcttttca    4415
Asp Val gatctgaatg gatagaacat c atg aac tta cac gaa tac cag gct aaa cag    4466
                         Met Asn Leu His Glu Tyr Gln Ala Lys Gln
                         1               5                   10 ctg ttt gca cgg tat ggc atg cca gca ccg acc ggc tac gcc tgt act    4514
Leu Phe Ala Arg Tyr Gly Met Pro Ala Pro Thr Gly Tyr Ala Cys Thr
                15                  20                  25 aca cca cgt gaa gca gaa gaa gcg gca tcg aaa atc ggt gca             4556
Thr Pro Arg Glu Ala Glu Glu Ala Ala Ser Lys Ile Gly Ala
        30                  35                  40
```

```
<210> SEQ ID NO 2
<211> LENGTH: 39
<212> TYPE: PRT
<213> ORGANISM: Pantoea ananatis

<400> SEQUENCE: 2

Ala Phe Ser Val Phe Arg Cys His Ser Ile Met Asn Cys Val Ser Val
 1               5                  10                  15

Cys Pro Lys Gly Leu Asn Pro Thr Arg Ala Ile Gly His Ile Lys Ser
            20                  25                  30

Met Leu Leu Gln Arg Ser Ala
        35

<210> SEQ ID NO 3
<211> LENGTH: 935
<212> TYPE: PRT
<213> ORGANISM: Pantoea ananatis

<400> SEQUENCE: 3

Met Gln Asn Ser Ala Met Lys Pro Trp Leu Asp Ser Ser Trp Leu Ala
 1               5                  10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Glu Gln Phe His Ser Ala Thr Arg Glu
    50                  55                  60

Tyr Phe Arg Arg Leu Ala Lys Asp Ala Ser Arg Tyr Thr Ser Ser Val
 65                  70                  75                  80

Thr Asp Pro Ala Thr Asn Ser Lys Gln Val Lys Val Leu Gln Leu Ile
                85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
    130                 135                 140

Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
                165                 170                 175

Asn Thr Glu Glu Lys Arg Trp Ile Gln Gln Arg Ile Glu Ser Gly Ala
            180                 185                 190

Ser Gln Thr Ser Phe Ser Gly Glu Glu Lys Lys Gly Phe Leu Lys Glu
        195                 200                 205

Leu Thr Ala Ala Glu Gly Leu Glu Lys Tyr Leu Gly Ala Lys Phe Pro
    210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
                245                 250                 255

Val Leu Gly Met Ala His Arg Gly Arg Leu Asn Val Leu Ile Asn Val
            260                 265                 270

Leu Gly Lys Lys Pro Gln Asp Leu Phe Asp Glu Phe Ser Gly Lys His
        275                 280                 285
```

-continued

Lys Glu His Leu Gly Thr Gly Asp Val Lys Tyr His Met Gly Phe Ser
    290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Met Gly Ser Val
                325                 330                 335

Arg Ala Arg Leu Asp Arg Leu Ala Glu Pro Val Ser Asn Lys Val Leu
                340                 345                 350

Pro Ile Thr Ile His Gly Asp Ala Ala Val Ile Gly Gln Gly Val Val
                355                 360                 365

Gln Glu Thr Leu Asn Met Ser Gln Ala Arg Gly Tyr Glu Val Gly Gly
    370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
                405                 410                 415

Val Leu Ala Pro Ile Phe His Val Asn Ala Asp Asp Pro Glu Ala Val
                420                 425                 430

Ala Phe Val Thr Arg Leu Ala Leu Asp Tyr Arg Asn Thr Phe Lys Arg
                435                 440                 445

Asp Val Phe Ile Asp Leu Val Cys Tyr Arg Arg His Gly His Asn Glu
450                 455                 460

Ala Asp Glu Pro Ser Ala Thr Gln Pro Leu Met Tyr Gln Lys Ile Lys
465                 470                 475                 480

Lys His Pro Thr Pro Arg Lys Ile Tyr Ala Asp Arg Leu Glu Gly Glu
                485                 490                 495

Gly Val Ala Ser Gln Glu Asp Ala Thr Glu Met Val Asn Leu Tyr Arg
                500                 505                 510

Asp Ala Leu Asp Ala Gly Glu Cys Val Val Pro Glu Trp Arg Pro Met
                515                 520                 525

Ser Leu His Ser Phe Thr Trp Ser Pro Tyr Leu Asn His Glu Trp Asp
                530                 535                 540

Glu Pro Tyr Pro Ala Gln Val Asp Met Lys Arg Leu Lys Glu Leu Ala
545                 550                 555                 560

Leu Arg Ile Ser Gln Val Pro Glu Gln Ile Glu Val Gln Ser Arg Val
                565                 570                 575

Ala Lys Ile Tyr Asn Asp Arg Lys Leu Met Ala Glu Gly Lys Ala
                580                 585                 590

Phe Asp Trp Gly Gly Ala Glu Asn Leu Ala Tyr Ala Thr Leu Val Asp
            595                 600                 605

Glu Gly Ile Pro Val Arg Leu Ser Gly Glu Asp Ser Gly Arg Gly Thr
    610                 615                 620

Phe Phe His Arg His Ala Val Val His Asn Gln Ala Asn Gly Ser Thr
625                 630                 635                 640

Tyr Thr Pro Leu His His Ile His Asn Ser Gln Gly Glu Phe Lys Val
                645                 650                 655

Trp Asp Ser Val Leu Ser Glu Glu Ala Val Leu Ala Phe Glu Tyr Gly
            660                 665                 670

Tyr Ala Thr Ala Glu Pro Arg Val Leu Thr Ile Trp Glu Ala Gln Phe
            675                 680                 685

Gly Asp Phe Ala Asn Gly Ala Gln Val Val Ile Asp Gln Phe Ile Ser
    690                 695                 700

Ser Gly Glu Gln Lys Trp Gly Arg Met Cys Gly Leu Val Met Leu Leu

```
                705                 710                 715                 720
Pro His Gly Tyr Glu Gly Gln Gly Pro Glu His Ser Ser Ala Arg Leu
                    725                 730                 735
Glu Arg Tyr Leu Gln Leu Cys Ala Glu Gln Asn Met Gln Val Cys Val
                740                 745                 750
Pro Ser Thr Pro Ala Gln Val Tyr His Met Leu Arg Arg Gln Ala Leu
                755                 760                 765
Arg Gly Met Arg Arg Pro Leu Val Val Met Ser Pro Lys Ser Leu Leu
            770                 775                 780
Arg His Pro Leu Ala Ile Ser Ser Leu Asp Glu Leu Ala Asn Gly Ser
785                 790                 795                 800
Phe Gln Pro Ala Ile Gly Glu Ile Asp Asp Leu Asp Pro Gln Gly Val
                    805                 810                 815
Lys Arg Val Val Leu Cys Ser Gly Lys Val Tyr Tyr Asp Leu Leu Glu
                820                 825                 830
Gln Arg Arg Lys Asp Glu Lys Thr Asp Val Ala Ile Val Arg Ile Glu
                835                 840                 845
Gln Leu Tyr Pro Phe Pro His Gln Ala Val Gln Glu Ala Leu Lys Ala
        850                 855                 860
Tyr Ser His Val Gln Asp Phe Val Trp Cys Gln Glu Pro Leu Asn
865                 870                 875                 880
Gln Gly Ala Trp Tyr Cys Ser Gln His His Phe Arg Asp Val Val Pro
                    885                 890                 895
Phe Gly Ala Thr Leu Arg Tyr Ala Gly Arg Pro Ala Ser Ala Ser Pro
                900                 905                 910
Ala Val Gly Tyr Met Ser Val His Gln Gln Gln Gln Gln Asp Leu Val
            915                 920                 925
Asn Asp Ala Leu Asn Val Asn
        930                 935

<210> SEQ ID NO 4
<211> LENGTH: 407
<212> TYPE: PRT
<213> ORGANISM: Pantoea ananatis

<400> SEQUENCE: 4

Met Ser Ser Val Asp Ile Leu Val Pro Asp Leu Pro Glu Ser Val Ala
  1               5                  10                  15
Asp Ala Thr Val Ala Thr Trp His Lys Lys Pro Gly Asp Ala Val Ser
                20                  25                  30
Arg Asp Glu Val Ile Val Glu Ile Glu Thr Asp Lys Val Val Leu Glu
            35                  40                  45
Val Pro Ala Ser Ala Asp Gly Val Leu Glu Ala Val Leu Glu Asp Glu
        50                  55                  60
Gly Ala Thr Val Thr Ser Arg Gln Ile Leu Gly Arg Leu Lys Glu Gly
65                  70                  75                  80
Asn Ser Ala Gly Lys Glu Ser Ser Ala Lys Ala Glu Ser Asn Asp Thr
                85                  90                  95
Thr Pro Ala Gln Arg Gln Thr Ala Ser Leu Glu Glu Glu Ser Ser Asp
                100                 105                 110
Ala Leu Ser Pro Ala Ile Arg Arg Leu Ile Ala Glu His Asn Leu Asp
            115                 120                 125
Ala Ala Gln Ile Lys Gly Thr Gly Val Gly Gly Arg Leu Thr Arg Glu
        130                 135                 140
```

```
Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
    210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
                245                 250                 255

Ser Ile Asp Gly Glu Asp Val Val Tyr His Asn Tyr Phe Asp Val Ser
            260                 265                 270

Ile Ala Val Ser Thr Pro Arg Gly Leu Val Thr Pro Val Leu Arg Asp
        275                 280                 285

Val Asp Ala Leu Ser Met Ala Asp Ile Glu Lys Ile Lys Glu Leu
    290                 295                 300

Ala Val Lys Gly Arg Asp Gly Lys Leu Thr Val Asp Leu Thr Gly
305                 310                 315                 320

Gly Asn Phe Thr Ile Thr Asn Gly Gly Val Phe Gly Ser Leu Met Ser
                325                 330                 335

Thr Pro Ile Ile Asn Pro Pro Gln Ser Ala Ile Leu Gly Met His Ala
            340                 345                 350

Ile Lys Asp Arg Pro Met Ala Val Asn Gly Gln Val Val Ile Leu Pro
        355                 360                 365

Met Met Tyr Leu Ala Leu Ser Tyr Asp His Arg Leu Ile Asp Gly Arg
    370                 375                 380

Glu Ser Val Gly Tyr Leu Val Ala Val Lys Glu Met Leu Glu Asp Pro
385                 390                 395                 400

Ala Arg Leu Leu Leu Asp Val
                405

<210> SEQ ID NO 5
<211> LENGTH: 40
<212> TYPE: PRT
<213> ORGANISM: Pantoea ananatis

<400> SEQUENCE: 5

Met Asn Leu His Glu Tyr Gln Ala Lys Gln Leu Phe Ala Arg Tyr Gly
1               5                   10                  15

Met Pro Ala Pro Thr Gly Tyr Ala Cys Thr Thr Pro Arg Glu Ala Glu
            20                  25                  30

Glu Ala Ala Ser Lys Ile Gly Ala
        35                  40

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
gtcgacaata gccygaatct gttctggtcg                                    30
```

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
aagcttatcg acgctcccct ccccaccgtt                              30

<210> SEQ ID NO 8
<211> LENGTH: 16214
<212> TYPE: DNA
<213> ORGANISM: Artificial Sequence
<220> FEATURE:
<223> OTHER INFORMATION: plasmid RSFCPG

<400> SEQUENCE: 8
gaattccgcc agaaccttca tcagcagcat aaacaggtgc agtgaacagc agagatacgg     60
ccagtgcggc caatgttttt tgtcctttaa acataacaga gtcctttaag gatatagaat    120
aggggtatag ctacgccaga atatcgtatt tgattattgc tagtttttag ttttgcttaa    180
aaaatattgt tagttttatt aaattggaaa actaaattat tggtatcatg aattgttgta    240
tgatgataaa tagggggg atatgataga cgtcattttc ataggttat aaaatgcgac       300
taccatgaag ttttttaattc aaagtattgg gttgctgata atttgagctg ttctattctt    360
tttaaatatc tatataggtc tgttaatgga ttttattttt acaagttttt tgtgtttagg    420
catataaaaa tcaagcccgc catatgaacg gcgggttaaa atatttacaa cttagcaatc    480
gaaccattaa cgcttgatat cgcttttaaa gtcgcgtttt tcatatcctg tatacagctg    540
acgcggacgg gcaatcttca taccgtcact gtgcatttcg ctccagtggg cgatccagcc    600
aacggtacgt gccattgcga aaatgacggt gaacatggaa gacggaatac ccatcgcttt    660
caggatgata ccagagtaga atcgacgtt cgggtacagt ttcttctcga taaagtacgg     720
gtcgttcagc gcgatgtttt ccagctccat agccacttcc agcaggtcat ccttcgtgcc    780
cagctctttc agcacttcat ggcaggtttc acgcattacg gtggcgcgcg ggtcgtaatt    840
tttgtacacg cggtgaccga gcccatcag gcggaaagaa tcattttgt ctttcgcacg      900
acgaaaaaat tccggaatgt gtttaacgga gctgatttct tccagcattt tcagcgccgc    960
ttcgttagca ccgccgtgcg caggtcccca cagtgaagca atacctgctg cgatacaggc   1020
aaacgggttc gcacccgaag agccagcggt acgcacggtg gaggtagagg cgttctgttc   1080
atggtcagcg tgcaggatca gaatacggtc catagcacgt tccagaatcg gattaacttc   1140
atacggttcg cacggcgtgg agaacatcat attcaggaag ttaccggcgt aggagagatc   1200
gttgcgcggg taaacaaatg gctgaccaat ggaatacttg taacacatcg cggccatggt   1260
cggcattttc gacagcaggc ggaacgcggc aatttcacgg tgacgaggat tgttaacatc   1320
cagcgagtcg tgatagaacg ccgccagcgc gccggtaata ccacacatga ctgccattgg   1380
atgcgagtcg cgacggaaag catggaacag acgggtaatc tgctcgtgga tcatggtatg   1440
acgggtcacc gtagttttaa attcgtcata ctgttcctga gtcggttttt caccattcag   1500
caggatgtaa caaacttcca ggtagttaga atcggtcgcc agctgatcga tcgggaaacc   1560
gcggtgcagc aaaataccct tcatcaccat caataaaagta attttagatt cgcaggatgc   1620
ggttgaagtg aagcctgggt caaaggtgaa cacacctttt gaaccgagag tacggatatc   1680

```
aataacatct tgacccagcg tgcctttcag cacatccagt tcaacagctg tatcccgtt    1740
gagggtgagt tttgcttttg tatcagccat ttaaggtctc cttagcgcct tattgcgtaa   1800
gactgccgga acttaaattt gccttcgcac atcaacctgg cttaccgt ttttatttg     1860
gctcgccgct ctgtgaaaga ggggaaaacc tgggtacaga gctctgggcg cttgcaggta   1920
aaggatccat tgatgacgaa taaatggcga atcaagtact tagcaatccg aattattaaa   1980
cttgtctacc actaataact gtcccgaatg aattggtcaa tactccacac tgttacataa   2040
gttaatctta ggtgaaatac cgacttcata acttttacgc attatatgct tttcctggta   2100
atgtttgtaa caactttgtt gaatgattgt caaattagat gattaaaaat taaataaatg   2160
ttgttatcgt gacctggatc actgttcagg ataaaacccg acaaactata tgtaggttaa   2220
ttgtaatgat tttgtgaaca gcctatactg ccgccagtct ccggaacacc ctgcaatccc   2280
gagccaccca gcgttgtaac gtgtcgtttt cgcatctgga agcagtgttt tgcatgacgc   2340
gcagttatag aaaggacgct gtctgacccg caagcagacc ggaggaagga aatcccgacg   2400
tcggggatcc tctagagctt tagcgtctga ggttatcgca atttggttat gagattactc   2460
tcgttattaa tttgctttcc tgggtcattt ttttcttgct taccgtcaca ttcttgatgg   2520
tatagtcgaa aactgcaaaa gcacatgaca taaacaacat aagcacaatc gtattaatat   2580
ataagggttt tatatctatg gatcagacat attctctgga gtcattcctc aaccatgtcc   2640
aaaagcgcga cccgaatcaa accgagttcg cgcaagccgt tcgtgaagta atgaccacac   2700
tctggccttt tcttgaacaa aatccaaaat atcgccagat gtcattactg gagcgtctgg   2760
ttgaaccgga gcgcgtgatc cagtttcgcg tggtatgggt tgatgatcgc aaccagatac   2820
aggtcaaccg tgcatggcgt gtgcagttca gctctgccat cggcccgtac aaaggcggta   2880
tgcgcttcca tccgtcagtt aacctttcca ttctcaaatt cctcggcttt gaacaaacct   2940
tcaaaaatgc cctgactact ctgccgatgg gcggtggtaa aggcggcagc gatttcgatc   3000
cgaaaggaaa aagcgaaggt gaagtgatgc gttttgcca ggcgctgatg actgaactgt    3060
atcgccacct gggcgcggat accgacgttc cggcaggtga tatcgggtt ggtggtcgtg    3120
aagtcggctt tatggcgggg atgatgaaaa agctctccaa caataccgcc tgcgtcttca   3180
ccggtaaggg cctttcattt ggcggcagtc ttattcgccc ggaagctacc ggctacggtc   3240
tggtttattt cacagaagca atgctaaaac gccacgtat gggttttgaa gggatgcgcg    3300
tttccgtttc tggctccggc aacgtcgccc agtacgctat cgaaaaagcg atggaatttg   3360
gtgctcgtgt gatcactgcg tcagactcca gcggcactgt agttgatgaa gcggattca    3420
cgaaagagaa actggcacgt cttatcgaaa tcaaagccag ccgcgatggt cgagtggcag   3480
attacgccaa agaatttggt ctggtctatc tcgaaggcca acagccgtgg tctctaccgg   3540
ttgatatcgc cctgccttgc gccacccaga tgaactgga tgttgacgcc gcgcatcagc   3600
ttatcgctaa tggcgttaaa gccgtcgcg aaggggcaaa tatgccgacc accatcgaag    3660
cgactgaact gttccagcag gcaggcgtac tatttgcacc gggtaaagcg ctaatgctg    3720
gtggcgtcgc tacatcgggc ctggaaatgc acaaaacgc tgcgcgcctg ggctggaaag    3780
ccgagaaagt tgacgcacgt ttgcatcaca tcatgctgga tatccaccat gcctgtgttg   3840
agcatggtgg tgaaggtgag caaaccaact acgtgcaggg cgcgaacatt gccggtttg    3900
tgaaggttgc cgatgcgatg ctggcgcagg gtgtgattta agttgtaaat gcctgatggc   3960
gctacgctta tcaggcctac aaatgggcac aattcattgc agttacgctc taatgtaggc   4020
cgggcaagcg cagcgccccc ggcaaaattt caggcgttta tgagtattta acggatgatg   4080
```

```
ctccccacgg aacatttctt atgggccaac ggcatttctt actgtagtgc tcccaaaact    4140
gcttgtcgta acgataacac gcttcaagtt cagcatccgt taactttctg cggactcacg    4200
cgcgcagcac tatgccagta aagaaatccc atttgactat tttttgata atcttcttcg    4260
cttttcgaaca actcgtgcgc ctttcgagaa gctagagtcg actcgccaat caccagcact    4320
aaagtgcgcg gttcgttacc cgattcatct ttgaaattag ccagtggcgg caaggcatta    4380
ttttcattca gtaactttgt tagcgagttt agttgctgac gatactgata atagccggtc    4440
aggaattgcc acggtgcggc aggctccata cgcgaggcca ggttatccaa cgttttctca    4500
aacggcttgt ttttgataaa cgtattcatg gcgatcggat gcagaatcaa gccataaagc    4560
agggcaaaag agacaacata acgccacggc tttggaatat agaccgggcg caggcgtgtc    4620
cacagcagaa ctgccaccgc cgtataggcc agcgcgataa gcacaatttt caggctgaaa    4680
tactggctta aatactcgct ggcttcgttg gtgttggttt cgaacatcac aaacagaacg    4740
ctctgcgaga actcctgacc gtagatgacg tagtagcaca gcgccgccag agaggccgcc    4800
catagccacca cgccgattac tgcggcaata attttaatcc gcttcggaaa gaggaatacc    4860
gggatcaacc acagcgaact gaataacagc gagtcgcgaa tgccgttagt gccactataa    4920
ccactgatgt aaataatggc ctgtagcaga gtagagaaaa accaaaagta gagcagtgcc    4980
caacccaggg ctttccagct aaaaagaggt ttagcctgga cttctgtgga atgcatagta    5040
agaacctgtc ttgaaaaaat atcgccgaat gtaacgacaa ttccttaagg atatctgaag    5100
gtatattcag aatttgaata aaatgcagac agaaatatat tgaaacgag ggtgttagaa    5160
cagaagtatt tcagaaaacc ctcgcgcaaa agcacgaggg tttgcagaag aggaagatta    5220
gccggtatta cgcatacctg ccgcaatccc ggcaatagtg accattaacg cttgttcgac    5280
gcgaggatcc ggttcctggc cttctttttc tgcctggcgg gagcggtgca gcaactcggc    5340
ctgcaatacg ttcagcgggt cggtgtaaat attccgtagc tgaatagact ctgcaatcca    5400
cggcagatcg gccatcagat gggaatcgtt ggcaatcgcc agcaccactt tgatgtcttc    5460
ttcttgcagg ttgcgtaact cttttacctaa cggccacagt gctttgtcta ccaggcgttg    5520
gtcatagtat tccgccagcc acaggtctgc tttggcgaag accatctcca gcatgccgag    5580
acgcgtcgag aagaatggcc aatcgcggca catagcctcc agctcgctct gtttgccgtc    5640
ttcgaccact ttttgcagcg ccgtacctgc acccagccag gcggggagca tcagacggtt    5700
ttgcgtccag gcgaagatcc acggaatggc gcgtagtgac tcgacgccgc cggttgggcg    5760
acgtttcgcc ggacgtgaac ccaacggcag tttgcccagt tcttgttccg gcgtagcgga    5820
gcggaagtaa ggcacaaaat ctttgttttc acgtacgtag ccgcggtaga catcgcagga    5880
gatgactgac agttcatcca taatgcgacg ccagctctct ttcggctccg gcggtggcag    5940
caggttggct tccagaatcg ccccggtata aagcgacagg ctgctgacgg tgatttctgg    6000
cagaccatat ttaaagcgga tcatctcgcc ctgttcggtt acgcgcaggc cgcctttcag    6060
gcttcctggc ggttgtgaca gcagcgccgc atgagcaggt gcgccgccgc gaccaatgga    6120
accgccgcga ccgtggaaca acgtcagctc aatacccgct ttttcgcagg ttttgattaa    6180
tgcatcctgt gcctgatatt gcgcccagga agctgccatc actcccgcat cttttgctga    6240
gtcggaatag ccaatcatca ccatctgttt gccctgaatc aggccacgat accagtcaat    6300
attgagcagc tgggtcatga catcgttggc gttgttcaga tcatcgaggg tttcaaacag    6360
cggagcaacc ggcatcgcaa acccgatacc cgcttctttc agcagcaggt ggacagccag    6420
```

```
tacgtcggac ggcgtttccg ccatcgagat cacgtaggcg gcaatggagc cttgcggtgc    6480
ttcggcaatc acctggcagg tatcgagcac ttcgcgcgtt tcggcgcttg gttgccagtt    6540
gcgcggcaga agcggacgtt tggagttcag ttcgcggatc aggaacgcct gtttgtcggc    6600
ctctgaccag ctttcgtagt cgccgatacc gaggtagcgg gtcagctcgc ccagcgcttc    6660
ggtatgacgc gtgctctcct gacggatatc aatacggacc agcggtacgc cgaaacattt    6720
cacgcggcgc agggtgtcga gcagatcgcc gttggcgata atacccatgc cacacgcctg    6780
aagtgactgg tagcaagcgt agagcggttc ccacagttct tcgttttgtg tcagcaggcc    6840
ttctggtttt ggcagttctt cgcctttcag gcgcgcttcc agccatgcct gtgtcgccat    6900
caggcgagaa cgcaggtttt tcatcagata gcgatacggt tctgcggcac cttcttcgcc    6960
aaccagcgcc agcagttcag gggtcgcttc aaccatcgac agttcagaaa ccagcacctg    7020
aatatctttc aggaacaaat cggtggcttt ccagcggctg agtagcagga cgtggcgggt    7080
gatatcggca gtgacgttcg ggttgccgtc gcggtcgccg cccatccacg aagtaaaacg    7140
gaccggaaca aattcgacgg gcagtttgta gccgaggttc tcttccagtt gttcgttcag    7200
ttcgcgcagg taatttggta cgccttgcca caggctgttt tccactacgg caaagcccca    7260
tttggcttca tctaccgggc ttggacgcag cttacggatt tcatcggtat gccatgactg    7320
ggcgatcaac tggcgcaggc gacgcatcag ctggttgtgt tcgtagtcag cgatatcttt    7380
gttatcgagc tgttttaaac aggcgttcac ttccaccatt ttgtggatca gtgtacgacg    7440
ggtaatttcg gttgggtgag ccgtgaggac cagttccagc gacagcgatt ccactgcttt    7500
tttgatggtg tcttcgctca gttccggctg gttttcagt ttacgcaggg tgcgggcgat    7560
cacttccggg ttgctggcag cttcgccttt cggcgaaatg ctgtggtatt gctcggcggt    7620
gttggccagg ttcaggaact gactaaacgc acgcgcaacg ggcagcagct cgtcgttcga    7680
caaattttgt aaggtggtga gcaactcctg gcggttagca tcattgccag cgcgtgaaga    7740
tttcgacaac ttacggatag tttctacgcg ttcaagaatg tgttctccca acgcatcctt    7800
gatggtttct cccagcactt tgccgagcat actgacatta ctacgcaatg cggaatattg    7860
ttcgttcata ttaccccaga cacccccatct tatcgtttga tagccctgta tccttcacgt    7920
cgcattggcg cgaatatgct cgggctttgc ttttcgtcgt cttttataaa gccacgtaaa    7980
agcggtgacg tcaaatgctg cgaaatcgct tcagcaaacg aataaatagc aggaatttac    8040
gtcattaaat tcacgacgct ttaaataagc gtaacttatg gaaatgttaa aaaatcgccc    8100
caagtaacac caaaggtgta ggtcggataa gatgcgcaag tatcgcatcc gacattattg    8160
cggcactgga gtttgcgaac agtgccggat gcggcgcgag cgccttatcc ggcctacagt    8220
tgggcatcgt ttgagtcact gtcggtcgga taagatgcgc aagtatcgca tccgacatta    8280
ttgcggcact ggagtttggc aacagtgccg gatgcggcgc gagcgcctta tccggcctac    8340
ggttgggcat cgtttgagtc actgtaggtc ggataagatg cgcaagcatc gcatccgaca    8400
ttattgcggc actggagttt ggcaacagcg ccggatgcgg cgcgagcgcc ttatccggcc    8460
tacgttttaa tgccagcaaa aatggtgaat tacctgggtt atcagttcgc gggtgggctt    8520
gataaaccgt gtttccagat attcatcagg ttgatgagcc tgattaattg agccaggccc    8580
caacaccagc gtcgggcata acgtttgaat aaacggcgct tcggtacagt agttcaccac    8640
ttcggttttt gctccgagca atttctcaac cacttcaacc agttgatgat tcggtgggca    8700
ttcatagcca gggatcggcg gatgcagctc gtcgacctgc aggagcagaa gagcatacat    8760
ctggaagcaa agccaggaaa gcggcctatg gagctgtgcg gcagcgctca gtaggcaatt    8820
```

-continued

```
tttcaaaata ttgttaagcc ttttctgagc atggtatttt tcatggtatt accaattagc    8880
aggaaaataa gccattgaat ataaaagata aaatgtctt gtttacaata gagtgggggg    8940
ggtcagcctg ccgccttggg ccgggtgatg tcgtacttgc ccgccgcgaa ctcggttacc    9000
gtccagccca gcgcgaccag ctccggcaac gcctcgcgca cccgctggcg gcgcttgcgc    9060
atggtcgaac cactggcctc tgacggccag acatagccgc acaaggtatc tatgaagcc     9120 ttgccggttt tgccggggtc gatccagcca cacagccgct ggtgcagcag gcgggcggtt    9180
tcgctgtcca gcgcccgcac ctcgtccatg ctgatgcgca catgctggcc gccacccatg    9240
acggcctgcg cgatcaaggg gttcagggcc acgtacaggc gcccgtccgc ctcgtcgctg    9300
gcgtactccg acagcagccg aaaccctgc cgcttgcggc cattctgggc gatgatggat     9360
accttccaaa ggcgctcgat gcagtcctgt atgtgcttga gcgccccacc actatcgacc    9420
tctgccccga tttcctttgc cagcgcccga tagctacctt tgaccacatg gcattcagcg    9480
gtgacggcct cccacttggg ttccaggaac agccggagct gccgtccgcc ttcggtcttg    9540
ggttccgggc caagcactag gccattaggc ccagccatgg ccaccagccc ttgcaggatg    9600
cgcagatcat cagcgcccag cggctccggg ccgctgaact cgatccgctt gccgtcgccg    9660
tagtcatacg tcacgtccag cttgctgcgc ttgcgctcgc cccgcttgag ggcacggaac    9720
aggccggggg ccagacagtg cgccgggtcg tgccggacgt ggctgaggct gtgcttgttc    9780
ttaggcttca ccacgggca cccccttgct cttgcgctgc ctctccagca cggcgggctt    9840
gagcaccccg ccgtcatgcc gcctgaacca ccgatcagcg aacggtgcgc catagttggc    9900
cttgctcaca ccgaagcgga cgaagaaccg gcgctggtcg tcgtccacac cccattcctc    9960
ggcctcggcg ctggtcatgc tcgacaggta ggactgccag cggatgttat cgaccagtac    10020
cgagctgccc cggctggcct gctgctggtc gcctgcgccc atcatggccg cgcccttgct    10080
ggcatggtgc aggaacacga tagagcaccc ggtatcggcg gcgatggcct ccatgcgacc    10140
gatgacctgg gccatgggc gcctggcgtt ttcttcctcg atgtggaacc ggcgcagcgt    10200
gtccagcacc atcaggcggc ggccctcggc ggcgcgcttg aggccgtcga accactccgg    10260
ggccatgatg ttgggcaggc tgccgatcag cggctggatc agcaggccgt cagccacggc    10320
ttgccgttcc tcgcgctga ggtgcgcccc aagggcgtgc aggcggtgat gaatggcggt     10380
gggcgggtct tcggcgggca ggtagatcac cgggccggtg ggcagttcgc ccacctccag    10440
cagatccggc ccgcctgcaa tctgtgcggc cagttgcagg gccagcatgg atttaccggc    10500
accaccgggc gacaccagcg ccccgaccgt accggccacc atgttgggca aaacgtagtc    10560
cagcggtggc ggcgctgctg cgaacgcctc cagaatattg ataggcttat gggtagccat    10620
tgattgcctc ctttgcaggc agttggtggt taggcgctgg cggggtcact accccgccc     10680 tgcgccgctc tgagttcttc caggcactcg cgcagcgcct cgtattcgtc gtcggtcagc    10740
cagaacttgc gctgacgcat ccctttggcc ttcatgcgct cggcatatcg cgcttggcgt    10800
acagcgtcag ggctggccag caggtcgccg gtctgcttgt ccttttggtc tttcatatca    10860
gtcaccgaga aacttgccgg ggccgaaagg cttgtcttcg cggaacaagg acaaggtgca    10920
gccgtcaagg ttaaggctgg ccatatcagc gactgaaaag cggccagcct cggccttgtt    10980
tgacgtataa ccaaagccac cgggcaacca atagcccttg tcactttga tcaggtagac    11040 cgaccctgaa gcgcttttt cgtattccat aaaaccccct tctgtgcgtg agtactcata    11100
gtataacagg cgtgagtacc aacgcaagca ctacatgctg aaatctggcc cgcccctgtc    11160
```

-continued

```
catgcctcgc tggcggggtg ccggtgcccg tgccagctcg gcccgcgcaa gctggacgct      11220
gggcagaccc atgaccttgc tgacggtgcg ctcgatgtaa tccgcttcgt ggcccgggctt    11280 gcgctctgcc agcgctgggc tggcctcggc catggccttg ccgatttcct cggcactgcg     11340
gccccggctg gccagcttct gcgcggcgat aaagtcgcac ttgctgaggt catcaccgaa     11400
gcgcttgacc agcccggcca tctcgctgcg gtactcgtcc agcgccgtgc gccggtggcg     11460
gctaagctgc cgctcgggca gttcgaggct ggccagcctg cgggccttct cctgctgccg     11520
ctgggcctgc tcgatctgct ggccagcctg ctgcaccagc gccgggccag cggtggcggt     11580
cttgcccttg gattcacgca gcagcaccca cggctgataa ccggcgcggg tggtgtgctt     11640
gtccttgcgg ttggtgaagc cgccaagcg gccatagtgg cggctgtcgg cgctggccgg      11700
gtcggcgtcg tactcgctgg ccagcgtccg gcaatctgc ccccgaagtt caccgcctgc      11760
ggcgtcggcc accttgaccc atgcctgata gttcttcggg ctggtttcca ctaccagggc     11820
aggctcccgg ccctcggctt tcatgtcatc caggtcaaac tcgctgaggt cgtccaccag     11880
caccagacca tgccgctcct gctcggcggg cctgatatac acgtcattgc cctgggcatt     11940
catccgcttg agccatggcg tgttctggag cacttcggcg gctgaccatt cccggttcat     12000
catctggccg gtggtggcgt ccctgacgcc gatatcgaag cgctcacagc ccatggcctt     12060
gagctgtcgg cctatggcct gcaaagtcct gtcgttcttc atcgggccac caagcgcagc    12120
cagatcgagc cgtcctcggt tgtcagtggc gtcaggtcga gcaagagcaa cgatgcgatc     12180
agcagcacca ccgtaggcat catggaagcc agcatcacgg ttagccatag cttccagtgc    12240
cacccccgcg acgcgctccg ggcgctctgc gcggcgctgc tcacctcggc ggctacctcc     12300
cgcaactctt tggccagctc cacccatgcc gcccctgtct ggcgctgggc tttcagccac    12360
tccgccgcct gcgcctcgct ggcctgctgg gtctggctca tgacctgccg ggcttcgtcg     12420
gccagtgtcg ccatgctctg ggccagcggt tcgatctgct ccgctaactc gttgatgcct    12480
ctggatttct tcactctgtc gattgcgttc atggtctatt gcctcccggt attcctgtaa    12540
gtcgatgatc tgggcgttgg cggtgtcgat gttcagggcc acgtctgccc ggtcggtgcg    12600
gatgccccgg ccttccatct ccaccacgtt cggcccccagg tgaacaccgg gcaggcgctc   12660
gatgccctgc gcctcaagtg ttctgtggtc aatgcgggcg tcgtggccag cccgctctaa    12720
tgcccggttg gcatggtcgg cccatgcctc gcgggtctgc tcaagccatg ccttgggctt    12780
gagcgcttcg gtcttctgtg ccccgcccctt ctccggggtc ttgccgttgt accgcttgaa    12840
ccactgagcg gcgggccgct cgatgccgtc attgatccgc tcggagatca tcaggtggca    12900
gtgcgggttc tcgccgccac cggcatggat ggccagcgta tacggcaggc gctcggcacc    12960
ggtcaggtgc tgggcgaact cggacgccag cgccttctgc tggtcgaggg tcagctcgac    13020
cggcagggca aattcgacct ccttgaacag ccgcccattg gcgcgttcat acaggtcggc    13080
agcatcccag tagtcggcgg gccgctcgac gaactccgg atgtgcccgg attcggcgtg     13140
caagacttca tccatgtcgc gggcatactt gccttcgcgc tggatgtagt cggccttggc    13200 cctgccgat tggccgcccg acctgctgcc ggttttcgcc gtaaggtgat aaatcgccat    13260
gctgcctcgc tgttgctttt gcttttcggc tccatgcaat ggccctcgga gagcgcaccg    13320
cccgaagggt ggccgttagg ccagtttctc gaagagaaac cggtaagtgc gccctcccct    13380
acaaagtagg gtcgggattg ccgccgctgt gcctccatga tagcctacga gacagcacat    13440
taacaatggg gtgtcaagat ggttaagggg agcaacaagg cggcggatcg gctggccaag    13500
ctcgaagaac aacgagcgcg aatcaatgcc gaaattcagc gggtgcgggc aagggaacag    13560
```

```
cagcaagagc gcaagaacga aacaaggcgc aaggtgctgg tgggggccat gattttggcc  13620
aaggtgaaca gcagcgagtg gccggaggat cggctcatgg cggcaatgga tgcgtacctt  13680
gaacgcgacc acgaccgcgc cttgttcggt ctgccgccac gccagaagga tgagccgggc  13740
tgaatgatcg accgagacag gccctgcggg gctgcacacg cgcccccacc cttcgggtag  13800
ggggaaaggc cgctaaagcg gctaaaagcg ctccagcgta tttctgcggg gtttggtgtg  13860
gggtttagcg ggctttgccc gccttcccc ctgccgcgca gcggtggggc ggtgtgtagc  13920
ctagcgcagc gaatagacca gctatccggc ctctggccgg gcatattggg caagggcagc  13980
agcgccccac aagggcgctg ataaccgcgc ctagtggatt attcttagat aatcatggat  14040
ggatttttcc aacaccccgc cagccccgc ccctgctggg tttgcaggtt tgggggcgtg  14100
acagttattg caggggttcg tgacagttat tgcaggggg cgtgacagtt attgcagggg  14160
ttcgtgacag ttagtacggg agtgacgggc actggctggc aatgtctagc aacggcaggc  14220
atttcggctg agggtaaaag aactttccgc taagcgatag actgtatgta aacacagtat  14280
tgcaaggacg cggaacatgc ctcatgtggc ggccaggacg gccagccggg atcgggatac  14340
tggtcgttac cagagccacc gacccgagca aaccettctc tatcagatcg ttgacgagta  14400
ttacccggca ttcgctgcgc ttatggcaga gcagggaaag gaattgccgg gctatgtgca  14460
acgggaattt gaagaatttc tccaatgcgg gcggctggag catggctttc tacgggttcg  14520
ctgcgagtct tgccacgccg agcacctggt cgctttcagc tgtaagcgtc gcggtttctg  14580
cccgagctgt ggggcgcggc ggatggccga aagtgccgcc ttgctggttg atgaagtact  14640
gcctgaacaa cccatgcgtc agtgggtgtt gagcttcccg tttcagctgc gtttcctgtt  14700
tggggtcgtt tgcgggaagg ggcggaatcc tacgctaagg cttttggccag cgatattctc  14760 cggtgagatt gatgtgttcc caggggatag gagaagtcgc ttgatatcta gtatgacgtc  14820
tgtcgcacct gcttgatcgc ggcccaaggg ttggtttgcg cattcacagt tctccgcaag  14880
aattgattgg ctccaattct tggagtggtg aatccgttag cgaggtgccg ccggcttcca  14940
ttcaggtcga ggtggcccgg ctccatgcac cgcgacgcaa cgcggggagg cagacaaggt  15000 ataggggcggc gcctacaatc catgccaacc cgttccatgt gctcgccgag gcggcataaa  15060
tcgccgtgac gatcagcggt ccagtgatcg aagttaggct ggtaagagcc gcgagcgatc  15120
cttgaagctg tccctgatgg tcgtcatcta cctgcctgga cagcatggcc tgcaacgcgg  15180
gcatcccgat gccgccggaa gcgagaagaa tcataatggg gaaggccatc cagcctcgcg  15240
tcgcgaacgc cagcaagacg tagcccagcg cgtcggccgc catgccggcg ataatggcct  15300
gcttctcgcc gaaacgtttg gtggcgggac cagtgacgaa ggcttgagcg agggcgtgca  15360
agattccgaa taccgcaagc gacaggccga tcatcgtcgc gctccagcga aagcggtcct  15420
cgccgaaaat gacccagagc gctgccggca cctgtcctac gagttgcatg ataaagaaga  15480
cagtcataag tgcggcgacg atagtcatgc cccgcgccca ccggaaggag ctgactgggt  15540
tgaaggctct caagggcatc ggtcgacgct ctcccttatg cgactcctgc attaggaagc  15600
agcccagtag taggttgagg ccgttgagca ccgccgccgc aaggaatggt gcatgcaagg  15660
agatggcgcc caacagtccc ccggccacgg ggcctgccac catacccacg ccgaaacaag  15720
cgctcatgag cccgaagtgg cgagcccgat cttccccatc ggtgatgtcg gcgatatagg  15780
cgccagcaac cgcacctgtg gcgccggtga tgccggccac gatgcgtccg gcgtagagga  15840
tccacaggac gggtgtggtc gccatgatcg cgtagtcgat agtggctcca agtagcgaag  15900
```

-continued

```
cgagcaggac tgggcggcgg ccaaagcggt cggacagtgc tccgagaacg ggtgcgcata    15960
gaaattgcat caacgcatat agcgctagca gcacgccata gtgactggcg atgctgtcgg    16020
aatggacgat atcccgcaag aggcccggca gtaccggcat aaccaagcct atgcctacag    16080
catccagggt gacggtgccg aggatgacga tgagcgcatt gttagatttc atacacggtg    16140
cctgactgcg ttagcaattt aactgtgata aactaccgca ttaaagctta tcgatgataa    16200
gctgtcaaac atga                                                      16214
```

<210> SEQ ID NO 9
<211> LENGTH: 427
<212> TYPE: PRT
<213> ORGANISM: Pantoea ananatis

<400> SEQUENCE: 9

```
Met Ala Asp Thr Lys Ala Lys Leu Thr Leu Asn Gly Asp Thr Ala Val
1               5                   10                  15

Glu Leu Asp Val Leu Lys Gly Thr Leu Gly Gln Asp Val Ile Asp Ile
            20                  25                  30

Arg Thr Leu Gly Ser Lys Gly Val Phe Thr Phe Asp Pro Gly Phe Thr
        35                  40                  45

Ser Thr Ala Ser Cys Glu Ser Lys Ile Thr Phe Ile Asp Gly Asp Glu
    50                  55                  60

Gly Ile Leu Leu His Arg Gly Phe Pro Ile Asp Gln Leu Ala Thr Asp
65                  70                  75                  80

Ser Asn Tyr Leu Glu Val Cys Tyr Ile Leu Leu Asn Gly Glu Lys Pro
                85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
    130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
        195                 200                 205

Pro Tyr Glu Val Asn Pro Ile Leu Glu Arg Ala Met Asp Arg Ile Leu
    210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
        275                 280                 285

Phe Arg Arg Ala Lys Asp Lys Asn Asp Ser Phe Arg Leu Met Gly Phe
    290                 295                 300

Gly His Arg Val Tyr Lys Asn Tyr Asp Pro Arg Ala Thr Val Met Arg
305                 310                 315                 320
```

```
Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
        355                 360                 365

Ile Leu Lys Ala Met Gly Ile Pro Ser Ser Met Phe Thr Val Ile Phe
    370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
                420                 425

<210> SEQ ID NO 10
<211> LENGTH: 447
<212> TYPE: PRT
<213> ORGANISM: Pantoea ananatis

<400> SEQUENCE: 10

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
                100                 105                 110

Gln Thr Phe Lys Asn Ala Leu Thr Thr Leu Pro Met Gly Gly Gly Lys
            115                 120                 125

Gly Gly Ser Asp Phe Asp Pro Lys Gly Lys Ser Glu Gly Glu Val Met
130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
```

```
                    260                 265                 270
Gly Phe Thr Lys Glu Lys Leu Ala Arg Leu Ile Glu Ile Lys Ala Ser
                275                 280                 285

Arg Asp Gly Arg Val Ala Asp Tyr Ala Lys Glu Phe Gly Leu Val Tyr
            290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
                355                 360                 365

Gly Lys Ala Ala Asn Ala Gly Gly Val Ala Thr Ser Gly Leu Glu Met
            370                 375                 380

Pro Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
                435                 440                 445

<210> SEQ ID NO 11
<211> LENGTH: 883
<212> TYPE: PRT
<213> ORGANISM: Pantoea ananatis

<400> SEQUENCE: 11

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190
```

-continued

Lys Leu Arg Pro Ser Pro Val Asp Glu Ala Lys Trp Gly Phe Ala Val
    195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro

```
            610             615             620
Glu Ile Thr Val Ser Ser Leu Ser Leu Tyr Thr Gly Ala Ile Leu Glu
625                 630                 635                 640

Ala Asn Leu Leu Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
                660                 665                 670

Arg Glu Asn Lys Asp Phe Val Pro Tyr Phe Arg Ser Ala Thr Pro Glu
            675                 680                 685

Gln Glu Leu Gly Lys Leu Pro Leu Gly Ser Arg Pro Ala Lys Arg Arg
690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
                740                 745                 750

Met Cys Arg Asp Trp Pro Phe Phe Ser Thr Arg Leu Gly Met Leu Glu
                755                 760                 765

Met Val Phe Ala Lys Ala Asp Leu Trp Leu Ala Glu Tyr Tyr Asp Gln
770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
                820                 825                 830

Asn Ile Tyr Thr Asp Pro Leu Asn Val Leu Gln Ala Glu Leu Leu His
                835                 840                 845

Arg Ser Arg Gln Ala Glu Lys Glu Gly Gln Glu Pro Asp Pro Arg Val
850                 855                 860

Glu Gln Ala Leu Met Val Thr Ile Ala Gly Ile Ala Ala Gly Met Arg
865                 870                 875                 880

Asn Thr Gly

<210> SEQ ID NO 12
<211> LENGTH: 6038
<212> TYPE: DNA
<213> ORGANISM: Artificial Sequence
<220> FEATURE:
<223> OTHER INFORMATION: plasmid pSTVCB
<220> FEATURE:
<221> NAME/KEY: CDS
<222> LOCATION: (2129)..(3439)

<400> SEQUENCE: 12
cgtatggcaa tgaaagacgg tgagctggtg atatgggata gtgttcaccc ttgttacacc      60
gttttccatg agcaaactga aacgttttca tcgctctgga gtgaatacca cgacgatttc     120
cggcagtttc tacacatata ttcgcaagat gtggcgtgtt acggtgaaaa cctggcctat     180
ttccctaaag ggtttattga gaatatgttt ttcgtctcag ccaatccctg ggtgagtttc     240
accagttttg atttaaacgt ggccaatatg gacaacttct tcgcccccgt tttcaccatg     300
ggcaaatatt atacgcaagg cgacaaggtg ctgatgccgc tggcgattca ggttcatcat     360
gccgtctgtg atggcttcca gtcggcagag atgcttaatg aattacaaca gtactgcgat     420
```

-continued

```
gagtggcagg gcggggcgta attttttttaa ggcagttatt ggtgcccttta aacgcctggt    480 gctacgcctg aataagtgat aataagcgga tgaatggcag aaattcgaaa gcaaattcga    540
cccggtcgtc ggttcagggc agggtcgtta aatagccgct tatgtctatt gctggtttac    600
cggtttattg actaccggaa gcagtgtgac cgtgtgcttc tcaaatgcct gaggccagtt    660
tgctcaggct ctccccgtgg aggtaataat tgacgatatg atcatttatt ctgcctccca    720
gagcctgata aaacggttta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccggggga ctgttgggcg ctgccggcac ctgtcctacg    900
agttgcatga taaagaagac agtcataagt gcggcgacga tagtcatgcc ccgcgcccac    960
cggaaggagc taccggacag cggtgcggac tgttgtaact cagaataaga aatgaggccg   1020
ctcatggcgt tccaatacgc aaaccgcctc tccccgcgcg ttggccgatt cattaatgca   1080
gctggcacga caggtttccc gactggaaag cgggcagtga gcgcaacgca attaatgtga   1140
gttagctcac tcattaggca ccccaggctt tacactttat gcttccggct cgtatgttgt   1200
gtggaattgt gagcggataa caatttcaca caggaaacag ctatgaccat gattacgcca   1260
agcttgcatg cctgcaggtc gactctagag gatccccgtc gacaatagcc tgaatctgtt   1320
ctggtcgaac cttggaaggt ccgcagccga acggccgtc gccagggatg aactcagagg   1380
gcagggtggg gaagtcggtc atgtcttcgg gcaactttct gcgcttggaa gtaaagggc    1440 cagggatcgt taacgatctg acccaacaac tataaccctg aagctgtcag ttcctagcac   1500
cctagattct tcacgcagtc tcccaaacga tgaaaaacgc ccaaaactgg cgacaccgaa   1560
ctattgaaaa cgcggggatt agttgaccag ccaccaattt gggggtagct caaagttttg   1620
caaagttttc aatttctagg ttgttaatat cccctgaggt tgcgttatag ggtggcgaat   1680
tgcatgggga aagctactcg gcacccatcc ttgtcgcgtg catcacaaac tttgctaaac   1740
tgtgcaccag tccacttatt gtgggatttt taatgcctta aaggccagca ttttttcaccc   1800 tctagcgggg ttgaatgctg gccttgaggg tgcagaacta aatagcagca catcggcaca   1860
attgatctga gttctattgg cgtgaccgtg gctactgatt acggtggctg tgggtggtcg   1920
ggaatgatgt aaccaacgtg attgtggggg aattggctct cacttcggat atggctaaac   1980
cgcatttatc ggtatagcgt gttaaccgga ccagattggg aaagaaatgt gtcgagtaac   2040
aaaaactgac atgcgcttgg cgcatcccag ttggtaagaa taaacgggac tacttccgta   2100
atccggaaga gttttttttcc gaacaaat atg ttt gaa agg gat atc gtg gct        2152
                                 Met Phe Glu Arg Asp Ile Val Ala
                                  1               5 act gat aac aac aag gct gtc ctg cac tac ccc ggt ggc gag ttc gaa       2200
Thr Asp Asn Asn Lys Ala Val Leu His Tyr Pro Gly Gly Glu Phe Glu
         10                  15                  20 atg gac atc atc gag gct tct gag ggt aac aac ggt gtt gtc ctg ggc       2248
Met Asp Ile Ile Glu Ala Ser Glu Gly Asn Asn Gly Val Val Leu Gly
     25                  30                  35                  40 aag atg ctg tct gag act gga ctg atc act ttt gac cca ggt tat gtg       2296
Lys Met Leu Ser Glu Thr Gly Leu Ile Thr Phe Asp Pro Gly Tyr Val
                 45                  50                  55 agc act ggc tcc acc gag tcg aag atc acc tac atc gat ggc gat gcg       2344
Ser Thr Gly Ser Thr Glu Ser Lys Ile Thr Tyr Ile Asp Gly Asp Ala
             60                  65                  70 gga atc ctg cgt tac cgc ggc tat gac atc gct gat ctg gct gag aat       2392
Gly Ile Leu Arg Tyr Arg Gly Tyr Asp Ile Ala Asp Leu Ala Glu Asn
         75                  80                  85
```

-continued

| | |
|---|---|
| gcc acc ttc aac gag gtt tct tac cta ctt atc aac ggt gag cta cca<br>Ala Thr Phe Asn Glu Val Ser Tyr Leu Leu Ile Asn Gly Glu Leu Pro<br>    90                           95                       100 | 2440 |
| acc cca gat gag ctt cac aag ttt aac gac gag att cgc cac cac acc<br>Thr Pro Asp Glu Leu His Lys Phe Asn Asp Glu Ile Arg His His Thr<br>105                      110                     115                   120 | 2488 |
| ctt ctg gac gag gac ttc aag tcc cag ttc aac gtg ttc cca cgc gac<br>Leu Leu Asp Glu Asp Phe Lys Ser Gln Phe Asn Val Phe Pro Arg Asp<br>                 125                   130                     135 | 2536 |
| gct cac cca atg gca acc ttg gct tcc tcg gtt aac att ttg tct acc<br>Ala His Pro Met Ala Thr Leu Ala Ser Ser Val Asn Ile Leu Ser Thr<br>    140                       145                     150 | 2584 |
| tac tac cag gac cag ctg aac cca ctc gat gag gca cag ctt gat aag<br>Tyr Tyr Gln Asp Gln Leu Asn Pro Leu Asp Glu Ala Gln Leu Asp Lys<br>               155                    160                   165 | 2632 |
| gca acc gtt cgc ctc atg gca aag gtt cca atg ctg gct gcg tac gca<br>Ala Thr Val Arg Leu Met Ala Lys Val Pro Met Leu Ala Ala Tyr Ala<br>   170                      175                   180 | 2680 |
| cac cgc gca cgc aag ggt gct cct tac atg tac cca gac aac tcc ctc<br>His Arg Ala Arg Lys Gly Ala Pro Tyr Met Tyr Pro Asp Asn Ser Leu<br>185                      190                     195                   200 | 2728 |
| aat gcg cgt gag aac ttc ctg cgc atg atg ttc ggt tac cca acc gag<br>Asn Ala Arg Glu Asn Phe Leu Arg Met Met Phe Gly Tyr Pro Thr Glu<br>                 205                   210                     215 | 2776 |
| cca tac gag atc gac cca atc atg gtc aag gct ctg gac aag ctg ctc<br>Pro Tyr Glu Ile Asp Pro Ile Met Val Lys Ala Leu Asp Lys Leu Leu<br>               220                    225                   230 | 2824 |
| atc ctg cac gct gac cac gag cag aac tgc tcc acc tcc acc gtt cgt<br>Ile Leu His Ala Asp His Glu Gln Asn Cys Ser Thr Ser Thr Val Arg<br>         235                     240                     245 | 2872 |
| atg atc ggt tcc gca cag gcc aac atg ttt gtc tcc atc gct ggt ggc<br>Met Ile Gly Ser Ala Gln Ala Asn Met Phe Val Ser Ile Ala Gly Gly<br>   250                      255                   260 | 2920 |
| atc aac gct ctg tcc ggc cca ctg cac ggt ggc gca aac cag gct gtt<br>Ile Asn Ala Leu Ser Gly Pro Leu His Gly Gly Ala Asn Gln Ala Val<br>265                      270                     275                   280 | 2968 |
| ctg gag atg ctc gaa gac atc aag agc aac cac ggt ggc gac gca acc<br>Leu Glu Met Leu Glu Asp Ile Lys Ser Asn His Gly Gly Asp Ala Thr<br>               285                    290                   295 | 3016 |
| gag ttc atg aac aag gtc aag aac aag gaa gac ggc gtc cgc ctc atg<br>Glu Phe Met Asn Lys Val Lys Asn Lys Glu Asp Gly Val Arg Leu Met<br>                 300                   305                   310 | 3064 |
| ggc ttc gga cac cgc gtt tac aag aac tac gat cca cgt gca gca atc<br>Gly Phe Gly His Arg Val Tyr Lys Asn Tyr Asp Pro Arg Ala Ala Ile<br>             315                    320                    325 | 3112 |
| gtc aag gag acc gca cac gag atc ctc gag cac ctc ggt ggc gac gat<br>Val Lys Glu Thr Ala His Glu Ile Leu Glu His Leu Gly Gly Asp Asp<br>  330                      335                   340 | 3160 |
| ctt ctg gat ctg gca atc aag ctg gaa gaa att gca ctg gct gat gat<br>Leu Leu Asp Leu Ala Ile Lys Leu Glu Glu Ile Ala Leu Ala Asp Asp<br>345                      350                     355                   360 | 3208 |
| tac ttc atc tcc cgc aag ctc tac ccg aac gta gac ttc tac acc ggc<br>Tyr Phe Ile Ser Arg Lys Leu Tyr Pro Asn Val Asp Phe Tyr Thr Gly<br>               365                    370                     375 | 3256 |
| ctg atc tac cgc gca atg ggc ttc cca act gac ttc ttc acc gta ttg<br>Leu Ile Tyr Arg Ala Met Gly Phe Pro Thr Asp Phe Phe Thr Val Leu<br>             380                    385                    390 | 3304 |
| ttc gca atc ggt cgt ctg cca gga tgg atc gct cac tac cgc gag cag<br>Phe Ala Ile Gly Arg Leu Pro Gly Trp Ile Ala His Tyr Arg Glu Gln | 3352 |

-continued

```
               395                 400                 405
ctc ggt gca gca ggc aac aag atc aac cgc cca cgc cag gtc tac acc    3400
Leu Gly Ala Ala Gly Asn Lys Ile Asn Arg Pro Arg Gln Val Tyr Thr
        410                 415                 420 ggc aac gaa tcc cgc aag ttg gtt cct cgc gag gag cgc taaatttagc    3449
Gly Asn Glu Ser Arg Lys Leu Val Pro Arg Glu Glu Arg
425                 430                 435 ggatgattct cgttcaactt cggccgaagc cacttcgtct gtcataatga cagggatggt    3509
ttcggccgtt tttgcatgaa accaaaaaat acgattttca aggagcatgt acagcacatg    3569
gaaaagccac agattgagct accggtcggt ccagcaccgg aagatctcgt aatctctgac    3629
atcatcgttg gcgaaggagc agaagcccgc ccaggtggag aagttgaggt ccactatgtg    3689
ggcgttgact ttgaaaccgg cgaggagttt gactcttcct gggatcgtgg acagaccagc    3749
cagttcccac tcaacggcct cattgcaggt tggcaagagg gaattccagg catgaaggtc    3809
ggcggacgtc gtcagctgac cattccgcca gaggctgctt acggccctga gggttccggc    3869
cacccactgt ctggccgtac cctggtgttc atcatcgatt tgatcagcgc ataatttctc    3929
ttactgcgct aaacgctcaa atcgtgtgaa gcgactgtcg cgtcccgccc tctccggatt    3989
gttatccaat tcggagaggg cgttgctgat tgtgccgaga atttcttcaa caaagtgctc    4049
ggtttcggcg acgatcccgt cgataagccc ttggcttaaa agtgcgtgcg cctgcacgcc    4109
ttgtcgctct atgatttccg cggcgtggtt ggtgtcgcgg aagaggatgg ccgaggcgcc    4169
ctctggtggc aatgcggaca gccacgcgtt ttcggccgcg tagaccagat cggcgggcag    4229
catggccagc gcgccaccgc caacgccctg accaataatg accgaaacgg tggggagggg    4289
agcgtcgata agcttgcatg cctgcaggtc gactctagag gatccccggg taccgagctc    4349
gaattcactg gccgtcgttt tacaacgtcg tgactgggaa aaccctggcg ttacccaact    4409
taatcgcctt gcagcacatc ccctttcgc cagctggcgt aatagcgaag aggcccgcac    4469
cgatcgccct tcccaacagt tgcgcagcct gaatggcgaa tgagcttatc gatgataagc    4529
tgtcaaacat gagaattaca acttatatcg tatggggctg acttcaggtg ctacatttga    4589
agagataaat tgcactgaaa tctagaaata ttttatctga ttaataagat gatcttcttg    4649
agatcgtttt ggtctgcgcg taatctcttg ctctgaaaac gaaaaaaccg ccttgcaggg    4709 cggttttttcg aaggttctct gagctaccaa ctctttgaac cgaggtaact ggcttggagg    4769
agcgcagtca ccaaaacttg tcctttcagt ttagccttaa ccggcgcatg acttcaagac    4829
taactcctct aaatcaatta ccagtggctg ctgccagtgg tgcttttgca tgtctttccg    4889
ggttggactc aagacgatag ttaccggata aggcgcagcg gtcggactga acgggggtt    4949 cgtgcataca gtccagcttg gagcgaactg cctacccgga actgagtgtc aggcgtggaa    5009
tgagacaaac gcggccataa cagcggaatg acaccggtaa accgaaaggc aggaacagga    5069
gagcgcacga gggagccgcc aggggaaacg cctggtatct ttatagtcct gtcgggtttc    5129
gccaccactg atttgagcgt cagatttcgt gatgcttgtc agggggcgg agcctatgga    5189 aaaacggctt tgccgcggcc ctctcacttc cctgttaagt atcttcctgg catcttccag    5249
gaaatctccg ccccgttcgt aagccatttc cgctcgccgc agtcgaacga ccgagcgtag    5309
cgagtcagtg agcgaggaag cggaatatat cctgtatcac atattctgct gacgcaccgg    5369
tgcagccttt tttctcctgc cacatgaagc acttcactga caccctcatc agtgccaaca    5429
tagtaagcca gtatacactc cgctagcgct gatgtccggc ggtgcttttg ccgttacgca    5489
ccaccccgtc agtagctgaa caggagggac agctgataga aacagaagcc actggagcac    5549
```

```
ctcaaaaaca ccatcataca ctaaatcagt aagttggcag catcacccga cgcactttgc    5609
gccgaataaa tacctgtgac ggaagatcac ttcgcagaat aaataaatcc tggtgtccct    5669
gttgataccg ggaagccctg ggccaacttt tggcgaaaat gagacgttga tcggcacgta    5729
agaggttcca actttcacca taatgaaata agatcactac cgggcgtatt ttttgagtta    5789
tcgagatttt caggagctaa ggaagctaaa atggagaaaa aaatcactgg atataccacc    5849
gttgatatat cccaatggca tcgtaaagaa cattttgagg catttcagtc agttgctcaa    5909
tgtacctata accagaccgt tcagctggat attacggcct ttttaaagac cgtaaagaaa    5969
aataagcaca agttttatcc ggcctttatt cacattcttg cccgcctgat gaatgctcat    6029
ccggaattt                                                            6038
```

<210> SEQ ID NO 13
<211> LENGTH: 437
<212> TYPE: PRT
<213> ORGANISM: Brevibacterium lactofermentum

<400> SEQUENCE: 13

```
Met Phe Glu Arg Asp Ile Val Ala Thr Asp Asn Asn Lys Ala Val Leu
 1               5                  10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
```

-continued

```
            275                 280                 285
Ser Asn His Gly Gly Asp Ala Thr Glu Phe Met Asn Lys Val Lys Asn
        290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
                340                 345                 350

Glu Glu Ile Ala Leu Ala Asp Asp Tyr Phe Ile Ser Arg Lys Leu Tyr
            355                 360                 365

Pro Asn Val Asp Phe Tyr Thr Gly Leu Ile Tyr Arg Ala Met Gly Phe
        370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
                420                 425                 430

Pro Arg Glu Glu Arg
            435
```

METHOD FOR PRODUCING L-GLUTAMIC ACID

The present invention claims priority under 35 U.S.C. §119 to Japanese Patent Application No. 2003-128722, filed May 7, 2003, and is a continuation under 35 U.S.C. §120 of PCT/JP2004/006031, filed May 7, 2004, the entirety of both of which is incorporated by reference.

BACKGROUND OF THE INVENTION

1. Field of the Invention

The present invention relates to a method for producing L-glutamic acid by fermentation. L-Glutamic acid is widely used as a raw material for production of seasonings and so forth.

2. Description of the Related Art

L-glutamic acid is mainly produced by fermentation using an L-glutamic acid-producing bacterium of the so-called coryneform bacterium belonging to the genus *Brevibacterium, Corynebacterium, Microbacterium,* or mutant strains thereof. Moreover, methods utilizing a microorganism belonging to the genera *Bacillus, Streptomyces, Penicillium, Pseudomonas, Arthrobacter, Serratia, Candida, Aerobacter aerogenes* (currently *Enterobacter aerogenes*), a mutant strain of *Escherichia coli*, or the like, are known. Furthermore, also known are methods of producing L-glutamic acid using a microorganism belonging to the genera *Klebsiella, Erwinia,* or *Pantoea* (U.S. Pat. No. 6,197,559), and methods of producing L-glutamic acid using an *Enterobacter* bacterium (U.S. Pat. No. 6,331,419).

Furthermore, various techniques for improving L-glutamic acid-producing ability by enhancing activities of L-glutamic acid biosynthetic enzymes through the use of recombinant DNA techniques have been disclosed. For example, it was reported that introduction of a gene encoding citrate synthase derived from *Escherichia coli* or *Corynebacterium glutamicum* was effective for enhancing L-glutamic acid-producing ability in bacterium belonging to the genus *Corynebacterium* or *Brevibacterium* (Japanese Patent Publication (Kokoku) No. 7-121228). In addition, Japanese Patent Laid-open (Kokai) No. 61-268185 discloses a cell harboring recombinant DNA containing a glutamate dehydrogenase gene derived from *Corynebacterium* bacteria. Furthermore, Japanese Patent Laid-open No. 63-214189 discloses a technique for increasing L-glutamic acid-producing ability by amplifying genes encoding glutamate dehydrogenase, isocitrate dehydrogenase, aconitate hydratase, and citrate synthase.

L-glutamic acid production has been considerably increased by the aforementioned breeding of microorganisms or the improving of production methods. However, in order to respond to an increased demand in the future, the development of methods which provide more efficient production of L-glutamic acid at a lower cost is still necessary, and therefore, still represent a need in the art.

Methods for L-glutamic acid fermentation while precipitating L-glutamic acid, which then accumulates in the culture broth, have been developed (European Patent Application Laid-open No. 1078989). Because the usual L-glutamic acid-producing bacteria cannot grow under acidic conditions, L-glutamic acid fermentation was conventionally performed under neutral conditions. Contrary to such conventional techniques, microorganisms which produce L-glutamic acid under acidic conditions were screened. As a result, it was reported that L-glutamic acid can be produced and accumulated in the medium while precipitating the L-glutamic acid by culturing the obtained microorganism (*Enterobacter agglomerans*) in a liquid medium in which pH was controlled so that L-glutamic acid is precipitated.

Furthermore, methods are known for producing L-glutamic acid by culturing such an L-glutamic acid-producing bacterium that can grow under acidic conditions, as described above, in a medium having a total content of organic acids that typically inhibit growth of the bacterium, but in an amount that does not inhibit the growth of the bacterium (European Patent Application Laid-open No. 1233070). Another known method includes a method for producing L-glutamic acid by culturing such a bacterium as described above at a first pH which is optimal for growth of the bacterium, and then culturing the bacterium at a second pH which is optimal for L-glutamic acid production by the bacterium, but is lower than the first pH (European Patent Application Laid-open No. 1233068).

Furthermore, a method is known for producing and accumulating L-glutamic acid in a medium while precipitating the L-glutamic acid into the medium, wherein crystals of L-glutamic acid are made to exist in the medium while the L-glutamic acid concentration in the medium is lower than the concentration at which natural crystallization of L-glutamic acid occurs (European Patent Application Laid-open No. 1233069).

The crystals of L-glutamic acid can exist in two forms, α- and β-form crystals (H. Takahashi, T. Takenishi, N. Nagashima, Bull. Chem. Soc. Japan, 35, 923 (1962); J. D. Bernal, Z. Krist., 78, 363 (1931); S. Hirokawa, Acta Cryst., 8, 637 (1955)). The β-form crystals are more stable in water, while the α-form crystals precipitate better, and are easier to handle in that, for example, the crystals can be effectively separated from a crystallized slurry. In the method described in European Patent Application Laid-open No. 1233069, the α-form crystals can be selectively crystallized when α-form crystals are used to induce the crystals of L-glutamic acid.

In addition, to lower the content of β-form crystals in L-glutamic acid crystals, methods of adding phenylalanine, leucine, tyrosine, cysteine, asparaginic acid, lysine, histidine, arginine, or alanine (Japanese Patent Publication (Kokoku) No. 36-17712, and Japanese Patent Publication (Kokoku) No. 38-16459), or adding ribonucleic acid, carboxy methyl cellulose, pectin, polyacrylic acid or salts thereof, or alginic acid or salts thereof (Japanese Patent Publication (Kokoku) No. 45-11286) have been disclosed. Those methods, however, have only been examined at the isoelectric point (pH 3.2) of L-glutamic acid, and no effect has been reported at a slightly higher pH, such as approximately pH 4.5.

SUMMARY OF THE INVENTION

An object of the present invention is to provide an improved method for producing L-glutamic acid using a microorganism such as a bacterium belonging to the genus *Pantoea* which has an L-glutamic acid-producing ability.

The inventors of the present application found that super solubility of L-glutamic acid can be increased by adding L-lysine to the medium during production of L-glutamic acid by fermentation. During fermentation, L-glutamic acid is also precipitated into the culture medium, which can result in selective crystallization of α-form crystals of L-glutamic acid in the medium when the concentration of L-lysine is at least at a certain level. Furthermore, while inducing the formation of crystals of L-glutamic acid in the medium, the amount of L-glutamic acid in the medium is equal to or higher than the saturation concentration, and is lower than the concentration at which natural crystallization of L-glutamic acid occurs. However, the inventors of the present invention found that the time frame of the crystallization can be lengthened by increasing the super solubility of L-glutamic acid.

It is an object of the present invention to provide a method for producing L-glutamic acid by fermentation comprising culturing a microorganism in a liquid medium within a pH range which is controlled so that L-glutamic acid precipitates, wherein said medium contains a carbon source able to be metabolized by said microorganism when the medium is at least saturated with L-glutamic acid, and adding L-lysine to the medium when L-glutamic acid concentration is lower than the concentration at which natural crystallization of L-glutamic acid occurs, and collecting α-form crystals of L-glutamic acid.

It is a further object of the invention to provide the method as described above, wherein the microorganism belongs to the genus *Pantoea*.

It is a further object of the invention to provide the method as described above, wherein the microorganism is *Pantoea ananatis*.

It is a further object of the invention to provide the method as described above, wherein L-lysine is added to a concentration of 900 mg/L or more.

It is a further object of the invention to provide the method as described above, wherein the pH of the medium at or after the addition of L-lysine is 3.0 to 5.0.

It is a further object of the invention to provide the method as described above, wherein inducing the formation of said α-form crystals of the L-glutamic acid in the medium occurs before natural crystallization of said L-glutamic acid.

DESCRIPTION OF THE PREFERRED EMBODIMENTS

Figure 1:
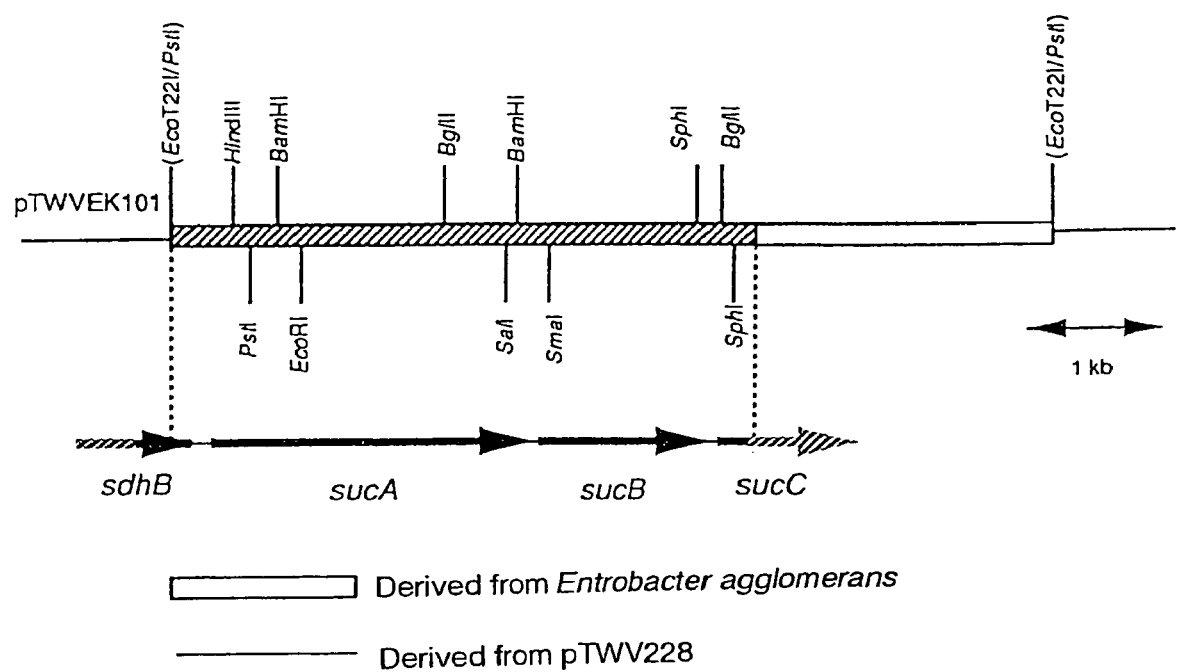
FIG. 1 shows a restriction map of a DNA fragment of pTWVEK101 derived from *Pantoea ananatis*.

Hereinafter, the present invention will be explained in detail.

The present invention is a method for producing L-glutamic acid by fermentation by culturing in a liquid medium under a pH which is controlled so that L-glutamic acid is precipitated, a microorganism that can metabolize a carbon source at a specific pH, wherein said medium contains the carbon source and L-glutamic acid at a saturation concentration, and wherein said microorganism is able to cause accumulation of an amount of L-glutamic acid in a liquid medium having said pH, wherein said amount exceeds the amount of L-glutamic acid at said saturation concentration (henceforth also referred to as an "L-glutamic acid-accumulating microorganism") in a medium, wherein the method includes adding L-lysine to the medium when the L-glutamic acid concentration in the medium is lower than the concentration at which natural crystallization of L-glutamic acid occurs. This method results inselective precipitation of α-form crystals of L-glutamic acid.

The above L-glutamic acid-accumulating microorganism can be obtained, for example, as follows. A sample containing microorganisms is inoculated into a liquid medium containing L-glutamic acid at a saturation concentration, and a carbon source, at a specific pH, and a strain that metabolizes the carbon source is selected. Although the specific pH is not particularly limited, it is usually about 5.0 or less, preferably about 4.5 or less, further preferably about 4.3 or less. The L-glutamic acid-accumulating microorganism is used for production of L-glutamic acid by fermentation, while simultaneously precipitating L-glutamic acid. If the pH is too high, it is difficult for the microorganism to produce L-glutamic acid in an amount sufficient for precipitation to occur. Therefore, the pH is preferably in the aforementioned range.

If the pH of an aqueous solution containing L-glutamic acid is lowered, the solubility of L-glutamic acid significantly falls to around the pKa of the γ-carboxyl group (4.25, 25° C.). The solubility is the lowest at the isoelectric point (pH 3.2), and the amount of L-glutamic acid above saturation will be precipitated out of solution. While it depends on the composition of the medium, L-glutamic acid dissolves at 10-20 g/L at pH 3.2, 30-40 g/L at pH 4.0, and 50-60 g/L at pH 4.7, at about 30° C. Usually the pH does not need to be below 3.0, because the L-glutamic acid precipitating effect reaches its upper limit when the pH goes below a certain value. However, the pH may be 3.0 or less.

In addition, the expression that a microorganism "can metabolize a carbon source" means that the microorganism can proliferate, or can consume a carbon source even though it cannot proliferate. That is, it indicates that the microorganism catabolizes a carbon source such as sugars or organic acids. Specifically, for example, if a microorganism proliferates when it is cultured in a liquid medium saturated with L-glutamic acid at pH 5.0 to 4.0, preferably pH 4.5 to 4.0, more preferably pH 4.3 to 4.0, most preferably about pH 4.0, at an appropriate temperature, for example, 28° C., 37° C., or 50° C., for 2 to 4 days, then the microorganism is considered to be able to metabolize the carbon source in the medium. Furthermore, for example, if a microorganism consumes a carbon source under the above-recited condition (pH, temperature, and culture time) even though proliferation does not occur, then the microorganism is considered to be able to metabolize the carbon source in the medium.

The microorganism that can metabolize a carbon source includes a microorganism that can grow in the aforementioned liquid medium. The expression that a microorganism "can grow" means that it can proliferate, or it can produce L-glutamic acid even though it cannot proliferate. Specifically, for example, if a microorganism proliferates when it is cultured in a liquid medium saturated with L-glutamic acid at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then the microorganism is considered to be able to grow in the medium. Furthermore, for example, if a microorganism produces L-glutamic acid even though no proliferation occurs when it is cultured in a synthetic liquid medium saturated with L-glutamic acid at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then it is considered that the microorganism can grow in the medium.

The selection of a microorganism as described above may be repeated two or more times under the same conditions, or by changing the pH or the concentration of L-glutamic acid. Selection at an early stage can be performed in a medium containing L-glutamic acid below saturation, and subsequent selection can be performed in a medium containing L-glutamic acid at saturation. Furthermore, strains with favorable properties, such as a superior proliferation rate, may be selected.

The L-glutamic acid-accumulating microorganism is able to produce L-glutamic acid when above saturation of L-glutamic acid in a liquid medium, in addition to the properties described above. The pH of the aforementioned liquid medium is preferably the same as or close to that of the medium used to screen a microorganism having the aforementioned properties. Usually, a microorganism becomes more sensitive to high concentrations of L-glutamic acid as the pH is lowered. Therefore, although a higher pH is preferred due to the microorganism's resistance to L-glutamic acid, a low pH is preferred when producing L-glutamic acid with accompanying precipitation. To satisfy these conditions, the pH can be in the range of 3 to 5, preferably 4 to 5, more preferably 4 to 4.7, even more preferably 4 to 4.5, and particularly preferably 4.0 to 4.3.

Examples of the L-glutamic acid-accumulating microorganism or breeding materials thereof include, but are not limited to, microorganisms belonging to the genus *Pantoea, Enterobacter, Klebsiella, Serratia, Erwinia, Escherichia, Corynebacterium, Brevibacterium, Alicyclobacillus, Bacillus, Saccharomyces*, or the like. Of these, microorganisms belonging to the genus *Pantoea* are preferred. Hereinafter, the microorganism of the present invention will be explained mainly for microorganisms belonging to the genus *Pantoea*. However, the microorganism is not limited to those belonging to the genus *Pantoea*, and those belonging to other genera can be similarly used.

An example of a microorganism belonging to the *Pantoea* includes, but is not limited to, *Pantoea ananatis*, preferably *Pantoea ananatis* AJ13355. This strain was isolated from soil in Iwata-shi, Shizuoka, Japan, and can proliferate in a medium containing L-glutamic acid and a carbon source at a low pH.

The *Pantoea ananatis* AJ13355 strain was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 and received an accession number of FERM P-16644. It was then converted to an international deposit under the provisions of Budapest Treaty on Jan. 11, 1999 and received an accession number of FERM BP-6614.

The above strain was identified as *Enterobacter agglomerans* when it was isolated and deposited as the *Enterobacter agglomerans* AJ13355 strain. However, it was recently re-classified as *Pantoea ananatis* on the basis of nucleotide sequencing of 16S rRNA and so forth (see the examples section).

Although the strains AJ13356 and AJ13601 that were derived from AJ13355 strain were also deposited at the aforementioned depository as *Enterobacter agglomerans*, they are described as *Pantoea ananatis* in this specification.

The L-glutamic acid-accumulating microorganism may originally have L-glutamic acid-producing ability, or may have L-glutamic acid-producing ability imparted or increased by breeding through mutagenesis, recombinant DNA techniques, or the like.

The L-glutamic acid-producing ability can be imparted or increased by, for example, increasing an activity of an enzyme that catalyzes a biosynthetic reaction of L-glutamic acid. The L-glutamic acid-producing ability can also be increased by decreasing or eliminating the activity of an enzyme that catalyzes a reaction which branches off from the biosynthetic pathway of L-glutamic acid, and generates a compound other than L-glutamic acid.

Examples of the enzyme that catalyzes the biosynthetic reaction of L-glutamic acid include, but are not limited to, glutamate dehydrogenase (hereafter, also referred to as "GDH"), glutamine synthetase, glutamate synthase, isocitrate dehydrogenase, aconitate hydratase, citrate synthase (hereinafter, also referred to as "CS"), phosphoenolpyruvate carboxylase (hereinafter, also referred to as "PEPC"), pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase, and so forth. Of these enzymes, any combination of CS, PEPC, and GDH are preferred. Furthermore, it is preferred that the activities of all three of the enzymes, CS, PEPC, and GDH, are enhanced in the L-glutamic acid-accumulating microorganism. In particular, CS from *Brevibacterium lactofermentum* is preferred, because it is not subject to inhibition by α-ketoglutaric acid, L-glutamic acid, and NADH.

In order to enhance the activity of CS, PEPC, or GDH, for example, a gene encoding CS, PEPC, or GDH can be cloned on an appropriate plasmid and a host microorganism can be transformed with the obtained plasmid. The copy number of the gene encoding CS, PEPC, or GDH (hereinafter, abbreviated as "gltA gene", "ppc gene", and "gdhA gene", respectively) in the transformant can be increased, resulting in an increase in the activity of CS, PEPC, or GDH.

The cloned gltA, ppc, and gdhA genes are introduced into the aforementioned parent strain alone or randomly in combination. When two or three genes are introduced, they may be cloned on one plasmid and introduced into the host, or separately cloned onto two or three plasmids that can coexist, and then introduced into the host.

Two or more genes encoding the same enzyme, but derived from different microorganisms, may be introduced into the same host.

The plasmids described above are not particularly limited so long as they are autonomously replicable in a microorganism belonging to, for example, the genus *Pantoea* or the like. Examples of these plasmids include pUC19, pUC18, pBR322, pHSG299, pHSG298, pHSG399, pHSG398, RSF1010, pMW119, pMW118, pMW219, pMW218, pACYC177, pACYC184, and so forth. Vectors of phage DNA can also be used to introduce the aforementioned genes.

Transformation can be performed by, for example, the method of D. M. Morrison (Methods in Enzymology, 68, 326 (1979)), wherein permeability of the recipient bacterium cells is increased by treating the cells with calcium chloride (Mandel M. and Higa A., J. Mol. Biol., 53, 159 (1970)), electroporation (Miller J. H., "A Short Course in Bacterial Genetics", Cold Spring Harbor Laboratory Press, U.S.A., 1992), or the like.

The activity of CS, PEPC, or GDH can also be increased by introducing multiple copies of the gltA gene, the ppc gene, or the gdhA gene on chromosomal DNA of the aforementioned parent strain. In order to introduce multiple copy numbers of these genes into the chromosomal DNA of a bacterium belonging to the genus *Pantoea*, sequences can be used which are present on the chromosomal DNA in multiple copy number, such as a repetitive DNA and inverted repeats present at the end of a transposable element. Alternatively, multiple copies can be introduced into the chromosomal DNA by incorporating them into a transposon and transferring it. As a result, the copy number of the gltA gene, the ppc gene, or the gdhA gene in the transformant strain is increased, and thus the activity of CS, PEPC, or GDH is increased.

The source of the gltA gene, the ppc gene, or the gdhA gene can be any organism so long as it has the activity of CS, PEPC, or GDH. Examples of the organism preferably include, but are not limited to, bacteria, which are procaryote, belonging to the genus *Pantoea, Enterobacter, Klebsiella, Erwinia, Serratia, Escherichia, Corynebacterium, Brevibacterium*, or *Bacillus*. Specifically, *Escherichia coli, Brevibacterium lactofermentum*, and so forth are encompassed by the present invention. The gltA gene, the ppc gene, and the gdhA gene can be obtained from the chromosomal DNA of the microorganisms described above.

The gltA gene, the ppc gene, and the gdhA gene can be obtained using a mutant strain which is deficient in the activity of CS, PEPC, or GDH so that a DNA fragment is isolated that supplements its auxotrophy from the chromosomal DNA of the aforementioned microorganism. Furthermore, since the nucleotide sequences of these genes from bacteria belonging to the genera *Escherichia* and *Corynebacterium* are known (Biochemistry, 22, pp. 5243-5249, (1983); J. Biochem., 95, pp. 909-916, (1984); Gene, 27, pp. 193-199, (1984); Microbiology, 140, pp. 1817-1828, (1994); Mol. Gen. Genet., 218, pp. 330-339, (1989); Molecular Microbiology, 6, pp. 317-326, (1992)), they can also be obtained by PCR utilizing primers synthesized based on each nucleotide sequence and using the chromosomal DNA as a template. It is known that, in enterobacteria such as bacteria belonging to the genus *Enterobacter* or *Klebsiella*, introduction of a gltA gene from a coryneform bacterium is more effective for enhancing the L-glutamic acid-producing ability when compared with that of a gltA gene from a bacterium of the same species (European Patent Application Laid-open No. 0999282). The strains of *Pantoea ananatis* described herein are described as *Enterobacter agglomerans*.

The activity of CS, PEPC, or GDH can also be increased by enhancing the expression of the gltA gene, the ppc gene, or the gdhA gene, besides the aforementioned method of amplifying the genes. For example, the expression can be enhanced by replacing a promoter for the gltA gene, the ppc gene, or the gdhA gene with a stronger promoter. For example, the lac promoter, trp promoter, trc promoter, tac promoter, $P_R$ promoter, and $P_L$ promoter of the lamda phage, and so forth are known as strong promoters. The gltA gene, the ppc gene, and the gdhA gene which have had their respective native promoters replaced are then cloned into a plasmid and introduced into the host microorganism, or introduced into the chromosomal DNA of the host microorganism using repetitive DNA, inverted repeat, transposon, or the like.

The activity of CS, PEPC, or GDH can also be increased by replacing the promoter of the gltA gene, the ppc gene, or the gdhA gene on the chromosome with a stronger promoter (see WO87/03006 and Japanese Patent Application Laid-open No. 61-268183), or inserting a strong promoter upstream of the gene coding sequence (see Gene, 29, pp. 231-241 (1984)). Specifically, homologous recombination can be performed between the gltA gene, the ppc gene, or the gdhA gene for which the promoter is replaced with a stronger one or DNA containing a part thereof, and the corresponding gene on the chromosome.

Examples of the enzyme that catalyzes the reaction which branches off from the biosynthetic pathway of L-glutamic acid and generates a compound other than L-glutamic acid include α-ketoglutarate dehydrogenase (hereafter, also referred to as "αKGDH"), isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase, and so forth. Of these enzymes, αKGDH is preferred.

In order to decrease or eliminate the activities of the aforementioned enzymes in a microorganism belonging to the genus *Pantoea* or the like, mutations for decreasing or eliminating the intracellular activity of the enzymes can be introduced into the genes of the aforementioned enzymes by a usual mutagenesis treatment method or a genetic engineering method.

Examples of mutagenesis methods include, for example, methods utilizing irradiation with X-rays or ultraviolet rays, methods utilizing treatment with a mutagenesis agent such as N-methyl-N'-nitro-N-nitrosoguanidine, and so forth. The mutation may be introduced into the coding region for the enzyme or a region which regulates expression, such as a promoter.

Examples of genetic engineering methods include, for example, methods utilizing gene recombination, transduction, cell fusion, and so forth. For example, a drug resistance gene is inserted into a cloned target gene to prepare a gene that has lost its function (defective gene). Subsequently, this defective gene is introduced into a host microorganism, and the target gene on the chromosome is replaced with the aforementioned defective gene by utilizing homologous recombination (gene disruption).

The extent of any decrease in intracellular activity of the target enzyme can be confirmed by measuring the enzyme activity of a cell extract or a purified fraction thereof obtained from a candidate strain and comparing it with that of a wild-type strain. For example, the αKGDH activity can be measured by the method of Reed et al. (Reed L. J. and Mukherjee B. B., Methods in Enzymology, 13, pp. 55-61 (1969)).

Depending on the target enzyme, a target mutant strain can be selected based on a phenotype of the mutant strain. For example, a mutant strain wherein the αKGDH activity is eliminated or decreased cannot proliferate or shows a markedly reduced proliferation rate in a minimal medium containing glucose or a minimal medium containing acetic acid or L-glutamic acid as the exclusive carbon source under aerobic culture conditions. However, normal proliferation is enabled even under the same conditions by adding succinic acid or lysine, methionine, and diaminopimelic acid to a minimal medium containing glucose. By utilizing these phenomena as indicators, a mutant strain with decreased αKGDH activity or deficient in αKGDH activity can be selected.

A method for preparing an αKGDH gene-deficient strain of *Brevibacterium lactofermentum* by utilizing homologous recombination is described in detail in WO95/34672. Similar methods can be applied to other microorganisms.

Furthermore, techniques such as the cloning of genes and digestion and ligation of DNA, transformation, and so forth are described in detail in Molecular Cloning, 2nd Edition, Cold Spring Harbor Press (1989), and so forth.

A specific example of a mutant strain deficient in αKGDH activity obtained as described above includes *Pantoea ananatis* AJ13356. *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 and received an accession number of FERM P-16645. It was then converted to an international deposit under the provisions of Budapest Treaty on Jan. 11, 1999 and received an accession number of FERM BP-6615. The *Pantoea ananatis* AJ13356 is deficient in αKGDH activity as a result of disruption of the αKGDH-E1 subunit gene (sucA). This strain was identified as *Enterobacter agglomerans* when it was isolated and deposited as the *Enterobacter agglomerans* AJ13356 strain. However, it was recently re-classified as *Pantoea* ananatis on the basis of nucleotide sequencing of 16S rRNA and so forth (see the examples section).

When *Pantoea ananatis*, which is an example of the microorganism used in the present invention, is cultured in a medium containing a saccharide, mucus is extracellularly secreted, occasionally resulting in low operation efficiency. Therefore, in this case, it is preferable to use a mutant strain which has been mutated to secrete less mucus. Examples of such mutagenesis treatment include, for example, methods utilizing irradiation with X-ray or ultraviolet ray, methods utilizing treatment with a mutagenesis agent such as N-methyl-N'-nitro-N-nitrosoguanidine, and so forth. A mutant strain which secretes less mucus can be selected by inoculating mutagenized bacterial cells in a medium containing a saccharide, for example, an LB medium plate containing 5 g/L of glucose, culturing them by tilting the plate about 45 degrees, and selecting a colony that does not show a flow of mucus.

In the present invention, imparting or enhancing L-glutamic acid-producing ability, and imparting other favorable properties such as reducing mucus secretion as described above, can be carried out in any order.

As a gene used for the breeding of such L-glutamic acid-producing bacteria as described above, the nucleotide sequence of the sucA gene of *Pantoea ananatis* and the amino acid sequence of the αKGDH-E1 subunit encoded by the gene are shown SEQ ID NO: 1 and SEQ ID NO: 3, respectively.

Furthermore, the nucleotide sequence of the plasmid RSFCPG containing the gltA gene, gdhA gene, and ppc gene derived from *Escherichia coli* (see Reference Example 1) is shown in SEQ ID NO: 8. In SEQ ID NO: 8, the coding regions of the gltA gene, gdhA gene and ppc gene are shown at nucleotide numbers 1770 to 487 (encoded by the complementary strand), 2598 to 3941, and 7869 to 5218 (encoded by the complementary strand), respectively. The amino acid sequences of CS, GDH, and PEPC encoded by these genes are shown in SEQ ID NOS: 9, 10 and 11, respectively. Furthermore, the nucleotide sequence of plasmid pSTVCB containing the gltA gene derived from *Brevibacterium lactofermentum* (see Reference Example 1) and the amino acid sequence of CS encoded by this gene are shown in SEQ ID NO: 12 and SEQ ID NO: 13, respectively.

Other than the above-mentioned wild-type sequences, CS, GDH, and PEPC may have an amino acid sequence which includes substitution, deletion, insertion, addition, or inversion of one or more amino acid residues, but does not substantially degrade the activities of the enzymes. Although the number of amino acid residues which may be substituted, deleted, inserted, added, or inverted differs depending on the positions in the three-dimensional structures of the proteins or the types of amino acid residues, it may be specifically between 1 to 30, preferably between 1 to 20, more preferably between 1 to 10.

Examples of DNA coding for substantially the same protein or peptide as CS, GDH, or PEPC include DNA hybridizable with an open reading frame (ORF) of the nucleotide sequence shown in SEQ ID NO: 12 or 8, or a probe that can be prepared from the nucleotide sequence under stringent conditions and encodes a protein having the activity of CS, GDH, or PEPC. The "stringent conditions" referred to herein include conditions under which so-called specific hybrid is formed, and non-specific hybrid is not formed. For example, stringent conditions include conditions under which DNAs having high homology, for example, DNAs having homology of not less than 50%, preferably not less than 70%, more preferably not less than 90%, most preferably not less than 95%, hybridize with each other, but DNAs having homology lower than the above do not hybridize with each other. Alternatively, stringent conditions include conditions whereby DNAs hybridize with each other at a salt concentration typically used during washing in Southern hybridization, i.e., 1×SSC, 0.1% SDS, preferably 0.1×SSC, 0.1% SDS, at 60° C.

The ORF of the nucleotide sequence of SEQ ID NO: 12 or SEQ ID NO: 8 or a partial sequence thereof can also be used as a probe. Such a probe can be prepared by PCR using oligonucleotides based on the nucleotide sequence of SEQ ID NO: 8 or 12 as primers and a DNA fragment containing the nucleotide sequence of SEQ ID NO: 8 or 12 or a partial nucleotide sequence thereof as a template. When a DNA fragment having a length of about 300 bp is used as the probe, the washing conditions for the hybridization can be, for example, 2×SSC and 0.1% SDS at 50° C.

It is sufficient that the deletion-type sucA gene used for gene disruption is homologous to such a degree that it causes homologous recombination with the sucA gene on the chromosome of the object microorganism. Such homology is preferably not less than 85%, more preferably not less than 90%, particularly preferably not less than 95%. Moreover, DNAs hybridizable under stringent conditions may cause homologous recombination.

Specific examples of such a strain obtained as described above include the AJ13601 strain derived from the aforementioned *Pantoea ananatis* AJ13355 strain. This strain was obtained by selecting a low mucus-producing strain from the AJ13355 strain, disrupting the αKGDH gene, introducing the gltA, ppc and gdhA genes from *Escherichia coli*, and the gltA gene from *Brevibacterium lactofermentum*, selecting a strain which is resistant to L-glutamic acid at high concentration and low pH, and selecting a strain which shows superior growth and L-glutamic acid-producing ability.

By culturing the L-glutamic acid-producing microorganism in a liquid medium that is adjusted to a pH that allows precipitation of L-glutamic acid, L-glutamic acid can be produced while it is precipitated. The "conditions that allow precipitation of L-glutamic acid produced by the microorganism" referred to herein means conditions that allow precipitation of L-glutamic acid when the L-glutamic acid-producing microorganism produces L-glutamic acid. Although the pH of these conditions may vary depending on the L-glutamic acid-producing ability of the microorganism, it is usually 3 to 5, preferably 4.5 or less, more preferably 4 or less when the microorganism is a bacterium belonging to the genus Pantoea.

Furthermore, as for the aforementioned pH condition that allows precipitation of L-glutamic acid, the pH is determined under conditions which allow the L-glutamic acid-producing microorganism to metabolize a carbon source in a liquid medium which is saturated with L-glutamic acid, and thereby precipating the excess L-glutamic acid above saturation into the medium at that pH.

When an L-glutamic acid-producing microorganism is cultured under the above conditions, the α-form crystals can be selectively precipitated by adding L-lysine to the medium at the point during the culture when the concentration of L-glutamic acid is lower than the concentration at which natural crystallization occurs. When the L-glutamic acid-producing microorganism is cultured in the absence of L-lysine, the α-form crystals of L-glutamic acid exist as seed crystals in the medium, ensuring precipitation of the α-form crystals. On the other hand, with the method of the present invention, the α-form crystals can be precipitated by adding L-lysine to the medium, even without the addition of seed crystals.

L-lysine is added to the medium when the concentration of L-glutamic acid is lower than the concentration at which natural crystallization occurs. This is because it is difficult to precipitate the α-form crystals, even if L-lysine is added to the medium, after the β-form crystals naturally crystallize. Preferably, L-lysine is added once the culture solution is saturated or over-saturated with L-glutamic acid. In addition, L-lysine may be added to the medium before L-glutamic acid reaches saturation in the medium. Furthermore, L-lysine may be added to the medium by using a microorganism that produces L-lysine (for example, see WO96/06180).

The expression "natural crystallization" or "naturally crystallize" described above means that the production of L-glutamic acid by a microorganism leads to natural precipitation of L-glutamic acid as the medium becomes over-saturated with L-glutamic acid.

In the present invention, the amount of L-lysine which can be added to medium is 500 mg/L or more, typically 600 mg/L to 1500 mg/L, preferably 1000 mg/L or more, more preferably 1500 mg/L or more. In particular, when seed crystal is not present, the amount of L-lysine is 900 mg/L or more, preferably 1000 mg/L or more, more preferably 1500 mg/L or more.

The pH of the medium during the precipitation of crystals of L-glutamic acid may generally be equal to the pH for producing L-glutamic acid in the medium, but is preferably adjusted to 3.0 to 5.0, more preferably 3.0 to 4.9, particularly preferably 4.5 to 4.9.

Known methods of producing L-glutamic acid using an L-glutamic acid-producing microorganism while precipitating L-glutamic acid can be used in the present invention, except that L-lysine is added to the medium when the L-glutamic acid concentration in the medium is lower than the concentration at which natural crystallization of L-glutamic acid occurs (for example, Japanese Patent Laid-open No. 2001-333769 (European Patent Application Laid-open No. 1078989), Japanese Patent Laid-open No. 2002-238591 (European Patent Application Laid-open No. 1233070), Japanese Patent Laid-open No. 2002-238592 (European Patent Application Laid-open No. 1233068), and Japanese Patent Laid-Open No. 2002-238593 (European Patent Application Laid-open No. 1233069)).

For example, one of the preferred embodiments of the method of the present invention is to produce L-glutamic acid by culturing an L-glutamic acid-producing microorganism in a medium having a pH of 5.0 or less, and in which the total content of organic acids that inhibit the growth of the microorganism is such that the growth of the microorganism is not inhibited, and in which L-lysine is added to the medium when L-glutamic acid concentration in the medium is lower than the concentration at which natural crystallization of L-glutamic acid occurs (see Japanese Patent Laid-open No. 2002-238591 (European Patent Application Laid-open No. 1233070)). In this embodiment, the above-mentioned organic acids include an organic acid that inhibits the growth of the microorganism when at a certain concentration (usually 0.5 g/L or more) in the medium at the inhibitory pH, and it is usually an organic acid which has 1 to 3 carbons, i.e., formic acid, acetic acid, or propionic acid. The total content of the organic acid is preferably 0.4 g/L or less, more preferably 0.3 g/L or less, further preferably 0.2 g/L or less.

Another preferred embodiment of the method of the present invention is to produce L-glutamic acid by culturing an L-glutamic acid-producing microorganism at a first pH which is optimal for growth of the microorganism, and then culturing the microorganism at a second lower pH which is also optimal for production of L-glutamic acid by the microorganism, and adding L-lysine to the medium when the L-glutamic acid concentration in the medium is lower than the concentration at which natural crystallization of L-glutamic acid occurs (see Japanese Patent Laid-open No. 2002-238592 (European Patent Application Laid-open No. 1233068)).

Another preferred embodiment of the method of the present invention is to produce L-glutamic acid by culturing an L-glutamic acid-producing microorganism at a first pH at which the growth of the microorganism is not inhibited by the organic acids in the medium, and then culturing the microorganism at a second lower pH which is optimal for production of L-glutamic acid by the microorganism, and adding L-lysine to the medium when L-glutamic acid concentration in the medium is lower than the concentration at which natural crystallization of L-glutamic acid occurs (see Japanese Patent Laid-open No. 2002-238591 (European Patent Application Laid-open No. 1233070)).

The growth of an L-glutamic acid-producing bacterium is generally inhibited by an organic acid under acidic conditions, whereas the microorganism could consume an organic acid under neutral conditions (EP 1233070 A). Based on this property, by growing the cells at a neutral pH and then adjusting the pH to be acidic, it is possible to obtain higher productivity of L-glutamic acid, and various materials may be used as the sugar source.

In this embodiment, the "organic acid" means an organic acid that inhibits the growth of a microorganism when it exists at a certain concentration (usually 0.5 g/L or more) in a medium at the second pH, and it is typically one which has 1 to 3 carbons, i.e., formic acid, acetic acid, or propionic acid.

The first pH and the second pH are selected so that they are compatible with the chosen L-glutamic acid-producing bacterium. These pH values can be easily measured by those skilled in the art. For example, the pH at which the growth of a microorganism is not inhibited by an organic acid can be determined by culturing an L-glutamic acid-producing bacterium in a medium containing an organic acid adjusted to various pH values, measuring cell density based on absorbance or the like, and comparing the cell density with that of a L-glutamic acid-producing bacterium cultured under the same, but in the absence of the organic acid. The pH suitable for the production of L-glutamic acid refers to a pH at which L-glutamic acid is produced into a medium, determinable by culturing an L-glutamic acid-producing bacterium in media of various pH values. Specifically, it can be determined by measuring the amount of L-glutamic acid in media having various pH values and comparing them.

The first pH is not particularly limited so long as growth of the microorganism is not inhibited by the organic acid in the medium, but it is usually 5.0 to 8.0.

The second pH is preferably a pH at which the produced L-glutamic acid precipitates, usually 3.0 to 5.0. Preventing high concentrations of L-glutamic acid in the medium, and the concomitant reduction in productivity, can be avoided by culturing at the pH at which L-glutamic acid precipitates.

The first pH and the second pH may not be strictly constant, but may fluctuate during the culture, so long as the advantage of the present invention can be obtained.

The L-glutamic acid-producing bacterium produces L-glutamic acid even at the first pH, however, the produced L-glutamic acid further lowers the pH. Therefore, addition of an alkalizing substance to the medium may be necessary to maintain the pH at the first pH.

Although the alkalizing substance is not particularly limited so long as it does not adversely affect the growth of the L-glutamic acid-producing bacterium or L-glutamic acid production, ammonia gas is preferred.

The pH of the medium may be lowered from the first pH to the second pH by adding an acidic substance. However, the pH is lowered by L-glutamic acid produced during the culture as described above. Therefore, it is preferable to lower the pH of the medium from the first pH to the second pH by controlling the amount of the alkalizing substance added, and therefore the addition of the acidic substance can be omitted.

The culture at the first pH may be continued until the organic acid in the medium is depleted. "Depletion" means that the amount of the organic acid decreases to a level at which the growth of the L-glutamic acid-producing bacterium is not inhibited during the culture at the second pH. Such a level of the organic acid can be easily measured by those skilled in the art. For example, the level can be determined by culturing an L-glutamic acid-producing bacterium in media containing an organic acid at various concentrations at the second pH, measuring cell density of the L-glutamic acid-producing bacterium, and comparing the cell density with that of the L-glutamic acid-producing bacterium cultured under the same conditions, but in the absence of the organic acid. Generally, as the second pH becomes lower, the level of the organic acid also becomes lower.

A further preferred embodiment of the method of the present invention is to produce L-glutamic acid by fermentation by culturing an L-glutamic acid-accumulating bacterium in a medium whereby the pH is controlled so to also precipate L-glutamic acid, wherein L-lysine is added to the medium when the L-glutamic acid concentration in the medium is lower than the concentration at which natural crystallization of L-glutamic acid occurs, and α-form crystals of L-glutamic acid (seed crystals) are present in the medium before natural crystallization of L-glutamic acid occurs (see Japanese Patent Laid-open No. 2002-238593 (European Patent Application Laid-open No. 1233069)).

Inducing the presence of seed crystals in the medium is performed before the occurrence of natural crystallization of β-form crystals of L-glutamic acid. In addition, seed crystals may dissolve if the seed crystals are added before the medium reaches saturation with L-glutamic acid. Therefore, the seed crystals are preferably added once the L-glutamic acid concentration in the medium exceeds saturation, but before the occurrence of natural crystallization of L-glutamic acid. In the present invention, adding L-lysine to the medium to increase the L-glutamic acid concentration at which natural crystallization thereof occurs, lengthens the time frame during which seed crystals can be added.

Inducing the presence of α-form crystals of L-glutamic acid in the medium includes artificially providing crystals of L-glutamic acid. Examples of this include adding α-form crystals, dissolving a certain amount of L-glutamic acid in the medium at the start of the culture and decreasing pH during the culture to forcibly precipitate crystals, and so forth. The amount of α-form crystals in the medium is usually 0.01 to 10 g/L. The amount of L-glutamic acid crystals in the medium and the concentration of L-glutamic acid can be measured by methods well known to those skilled in the art. Crystals of L-glutamic acid are measured after the medium is left to stand, and the crystals are collected by decantation. The concentration of L-glutamic acid in the medium is the concentration of dissolved L-glutamic acid. When crystals precipitate in the medium, the concentration of L-glutamic acid indicates the L-glutamic acid concentration which is measured in a clear solution obtained by separating the solid content from the medium by centrifugation (or filtration).

It is preferable to add α-form crystals of L-glutamic acid to the culture medium.

The preferred amount of crystals to be added is usually 0.2 g/L or more. If the crystals are added in the aforementioned amount or a larger amount, α-form crystals can be obtained with good reproducibility. Crystals of α-form can be handled more easily as compared with crystals of the β-form in view of their morphology.

As the medium used for the present invention, a usual nutrient medium containing a carbon source, nitrogen source, and inorganic salts as well as organic trace amount nutrients such as amino acids and vitamins as required can be used, except that the pH is adjusted to satisfy the predetermined conditions. Either a synthetic or natural medium may be used. Any carbon source and nitrogen source that can be used by a strain to be cultured may be used in the medium.

Saccharides such as glucose, glycerol, fructose, sucrose, maltose, mannose, galactose, starch hydrolysate, and molasses are used as the carbon source. In addition, organic acids such as acetic acid and citric acid may be used alone or in combination with another carbon source.

Ammonia, ammonium salts such as ammonium sulfate, ammonium carbonate, ammonium chloride, ammonium phosphate, and ammonium acetate, nitrates and so forth are used as the nitrogen source.

Amino acids, vitamins, fatty acids, nucleic acids, and those containing these substances such as peptone, casamino acid, yeast extract, and soybean protein decomposition products are used as the organic trace nutrients. When an auxotrophic mutant strain that requires an amino acid and so forth for metabolization or growth is used, the required nutrient must be supplemented.

Phosphates, magnesium salts, calcium salts, iron salts, manganese salts, and so forth can be used as the inorganic salts.

As for the culture method, an aeration culture at 20 to 42° C. is usually performed provided that the pH is controlled to the predetermined value, preferably 3 to 5.

After completion of the culture, the L-glutamic acid which has precipitated in the culture can be collected by centrifugation, filtration, or the like. L-Glutamic acid dissolved in the medium can be also collected by known methods. For example, the L-glutamic acid can be isolated by concentrating the culture broth to crystallize it, or isolated by ion exchange chromatography, or the like. It is also possible to crystallize the L-glutamic acid which has dissolved in the medium and then collect the crystallized L-glutamic acid together with the L-glutamic acid which has precipitated during the culture.

In the embodiment whereby the L-glutamic acid which exceeds saturation precipitates, the concentration of L-glutamic acid dissolved in the medium is maintained at a constant level. Therefore, the effect of L-glutamic acid at a high concentration on microorganisms can be reduced. Accordingly, it also is possible to breed a microorganism which has further improved L-glutamic acid-producing ability. Furthermore, since L-glutamic acid is precipitated as crystals, acidification of the culture broth by high concentrations of L-glutamic acid is suppressed, and therefore the amount of alkali required for maintaining the pH of the culture broth can be significantly reduced.

EXAMPLES

Hereafter, the present invention will be more specifically explained with reference to the following non-limiting examples.

Reference Example 1

<1> Screening of Microorganism Having L-Glutamic Acid Resistance in Acidic Environment Screening of a microorganism having L-glutamic acid resistance in an acidic environment was performed as follows. One (1) g each of about 500 samples obtained from nature including soil, fruits, plant bodies, river water, and so forth was suspended in 5 mL of sterilized water, and 200 μL thereof was applied to 20 mL of solid medium adjusted to pH 4.0 with HCl. The composition of the medium was as follows: 3 g/L of glucose, 1 g/L of ammonium sulfate, 0.2 g/L of magnesium sulfate heptahydrate, 0.5 g/L of potassium dihydrogenphosphate, 0.2 g/L of sodium chloride, 0.1 g/L of calcium chloride dihydrate, 0.01 g/L of ferrous sulfate heptahydrate, 0.01 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, 50 μg/L of biotin, 50 μg/L of calcium pantothenate, 50 μg/L of folic acid, 50 μg/L of inositol, 50 μg/L of niacin, 50 μg/L of p-aminobenzoic acid, 50 μg/L of pyridoxine hydrochloride, 50 μg/L of riboflavin, 50 μg/L of thiamin hydrochloride, 50 mg/L of cycloheximide, and 20 g/L of agar.

The media plated with the above samples were incubated at 28° C., 37° C., or 50° C. for 2 to 4 days, and 378 colony-forming strains were obtained.

Subsequently, each of the strains obtained as described above was inoculated into a test tube of 16.5 cm in length and 14 mm in diameter which contained 3 mL of liquid medium (adjusted to pH 4.0 with HCl) containing L-glutamic acid at saturation concentration, and cultured at 28° C., 37° C., or 50° C. for 24 hours to 3 days with shaking. Then, the strains which grew were selected. The composition of the aforementioned medium was as follows: 40 g/L of glucose, 20 g/L of ammonium sulfate, 0.5 g/L of magnesium sulfate heptahydrate, 2 g/L of potassium dihydrogenphosphate, 0.5 g/L of sodium chloride, 0.25 g/L of calcium chloride dihydrate, 0.02 g/L of ferrous sulfate heptahydrate, 0.02 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, and 2 g/L of yeast extract.

Thus, 78 strains of microorganisms which demonstrated L-glutamic acid resistance in an acidic environment were successfully obtained.

<2> Selection of Strains Showing Superior Growth from Microorganisms Having L-Glutamic Acid Resistance in Acidic Environment The various microorganisms having L-glutamic acid resistance in an acidic environment obtained as described above are each inoculated into a test tube of 16.5 cm in length and 14 mm in diameter which contained 3 mL of medium (adjusted to pH 4.0 with HCl), wherein the medium was obtained by adding 20 g/L of glutamic acid and 2 g/L of glucose to M9 medium (Sambrook, J., Fritsh, E. F. and Maniatis, T., "Molecular Cloning", Cold Spring Harbor Laboratory Press, U.S.A., 1989), and the turbidity of the medium was measured over time to select strains with a favorable growth rate. As a result, the AJ13355 strain which was obtained from soil in Iwata-shi, Shizuoka, Japan showed favorable growth. This strain was determined to be *Enterobacter agglomerans* based on its bacteriological properties described above. *Enterobacter agglomerans* includes those re-classified as *Pantoea agglomerans*, *Pantoea ananatis*, *Pantoea stewartii*, and so forth on the basis of nucleotide sequence analysis of 16S rRNA or the like, and the AJ13355 strain is classified as *Pantoea ananatis*.

<3> Acquisition of Strain with Reduced Mucus Secretion from *Pantoea ananatis* AJ13355 Strain Since the *Pantoea ananatis* AJ13355 strain secretes mucus extracellularly when cultured in a medium containing a saccharide, operation efficiency is not favorable. Therefore, a strain with reduced mucus secretion was obtained by the ultraviolet irradiation method (Miller, J. H. et al., "A Short Course in Bacterial Genetics; Laboratory Manual", p. 150, 1992, Cold Spring Harbor Laboratory Press, U.S.A.).

The *Pantoea ananatis* AJ13355 strain was irradiated with ultraviolet rays for 2 minutes 60 cm away from a 60-W ultraviolet lamp and cultured in LB medium overnight to fix the mutation. The mutagenized strain was diluted and inoculated into LB medium containing 5 g/L of glucose and 20 g/L of agar so that about 100 colonies per plate emerged, and was cultured at 30° C. overnight while the plate was tilted at about 45 degrees, and then 20 colonies without mucus flow were selected.

The SC17 strain was selected from the strains selected above, since no revertant emerged even after subculturing 5 times in LB medium containing 5 g/L of glucose and 20 g/L of agar, and which grew equivalent to the parent strain in LB medium, wherein the LB medium contained 5 g/L of glucose and M9 medium (Sambrook, J. et al., Molecular Cloning, 2nd Edition, Cold Spring Harbor Press, U.S.A., 1989)

supplemented with 20 g/L of L-glutamic acid and 2 g/L of glucose and adjusted to pH 4.5 with HCl.

<4> Construction of Glutamic Acid-Producing Bacterium from *Pantoea ananatis* SC17 Strain (1) Preparation of αKGDH Deficient Strain from *Pantoea ananatis* SC17 Strain A strain that was deficient in αKGDH and had an enhanced L-glutamic acid biosynthetic system was prepared from the *Pantoea ananatis* SC17 strain.

(i) Cloning of αKGDH Gene (Hereinafter, Referred to as "sucAB") of *Pantoea ananatis* AJ13355 Strain The sucAB gene from the *Pantoea ananatis* AJ13355 strain was cloned by selecting a DNA fragment complementing the acetic acid-unassimilating property of the αKGDH-E1 subunit gene (hereinafter, referred to as "sucA")-deficient strain of *Escherichia coli* from the chromosomal DNA of the *Pantoea ananatis* AJ13355 strain.

The chromosomal DNA of the *Pantoea ananatis* AJ13355 strain was isolated by a method usually employed for extracting chromosomal DNA from *Escherichia coli* (Text for Bioengineering Experiments, Edited by the Society for Bioscience and Bioengineering, Japan, pp. 97-98, Baifukan, 1992). The pTWV228 (resistant to ampicillin), which is a commercial product of Takara Shuzo Co., Ltd, was used as a vector.

The chromosomal DNA of the AJ13355 strain which had been digested with EcoT22I, and pTWV228 which had been digested with PstI, were ligated using T4 ligase, and the ligation mixture was used to transform the sucA-deficient *Escherichia coli* JRG465 strain (Herbert, J. et al., Mol. Gen. Genetics, 105, 182 (1969)). A strain grown in an acetate minimal medium was selected from the transformant strains obtained above, and a plasmid was extracted from the obtained strain and designated pTWVEK101. The *Escherichia coli* JRG465 strain harboring pTWVEK101 recovered auxotrophy for succinic acid or L-lysine and L-methionine, besides having the trait of acetic acid-unassimilatability. This suggests that pTWVEK101 contained the sucA gene of *Pantoea ananatis*.

FIG. 1 shows a restriction enzyme map of a DNA fragment derived from *Pantoea* ananatis in pTWVEK101. SEQ ID NO: 1 is the result of sequencing the hatched portion in FIG. 1. In the nucleotide sequence, sequences considered to be two full length ORFs and two sequences considered to be partial sequences of ORFs were found. Each of SEQ ID NO: 2 to 5 shows the amino acid sequences which may be encoded by these ORFs or partial sequences thereof from the 5' end in order. As a result of a homology search for these, it was revealed that the portions of the determined nucleotide sequences contained a 3' end partial sequence of the succinate dehydrogenase iron-sulfur protein gene (sdhB), full length sucA, and αKGDH-E2 subunit gene (sucB gene), and a 5' end partial sequence of the succinyl CoA synthetase β subunit gene (sucC gene). When comparing the amino acid sequences deduced from these nucleotide sequences with those derived from *Escherichia coli* (Eur. J. Biochem., 141, pp. 351-359 (1984); Eur. J. Biochem., 141, pp. 361-374 (1984); Biochemistry, 24, pp. 6245-6252 (1985)), each of the amino acid sequences showed very high homology to each other. In addition, it was found that a cluster of sdhB-sucA-sucB-sucC was located on the chromosome of *Pantoea ananatis*, as in *Escherichia coli* (Eur. J. Biochem., 141, pp. 351-359 (1984); Eur. J. Biochem., 141, pp. 361-374 (1984); Biochemistry, 24, pp. 6245-6252 (1985)).

(ii) Acquisition of αKGDH-Deficient Strain Derived from *Pantoea ananatis* SC17 Strain The homologous recombination was performed using the sucAB gene of *Pantoea ananatis* obtained as described above to obtain an αKGDH-deficient strain of *Pantoea ananatis*.

After pTWVEK101 was digested with SphI to excise a fragment containing sucA, the fragment was blunt-ended with Klenow fragment (Takara Shuzo Co., Ltd.) and ligated with pBR322 which had been digested with EcoRI and blunt-ended with Klenow fragment using T4 DNA ligase (Takara Shuzo Co., Ltd.). The obtained plasmid was digested at the restriction enzyme BglII recognition site, located approximately at the center of sucA, by using the enzyme, blunt-ended with Klenow fragment, and then ligated again using T4 DNA ligase. It was thought that the sucA gene was unable to function due to the introduction of a frameshift mutation into sucA on the newly constructed plasmid during the above procedure.

The plasmid constructed as described above was digested with restriction enzyme ApaLI, and subjected to agarose gel electrophoresis. A DNA fragment containing sucA with a frameshift mutation and a tetracycline resistance gene derived from pBR322 was recovered. The recovered DNA fragment was ligated again using T4 DNA ligase to construct a plasmid to disrupt the αKGDH gene.

The plasmid for disrupting the αKGDH gene obtained as described above was used to transform the *Pantoea ananatis* SC17 strain by electroporation (Miller, J. H., "A Short Course in Bacterial Genetics; Handbook", p. 279, Cold Spring Harbor Laboratory Press, U.S.A., 1992), and a strain wherein sucA on the chromosome was replaced with the mutant sucA of the plasmid by homologous recombination was obtained using tetracycline resistance as a marker. This strain was designated SC17sucA.

In order to confirm that the SC17sucA strain was deficient in αKGDH activity, the enzyme activity was measured by the method of Reed et al. (Reed, L. J. and Mukherjee, B. B., Methods in Enzymology, 13, pp. 55-61, (1969)) using cells cultured in LB medium to the logarithmic growth phase. As a result, αKGDH activity of 0.073 (ΔABS/min/mg protein) was detected from the SC17 strain, whereas no αKGDH activity was detected from the SC17sucA strain, and thus it was confirmed that the sucA was eliminated as intended.

(2) Enhancement of L-Glutamic Acid Biosynthesis System of *Pantoea ananatis* SC17sucA Strain Subsequently, the citrate synthase gene, phosphoenolpyruvate carboxylase gene, and glutamate dehydrogenase gene from *Escherichia coli* were introduced into the SC17sucA strain.

(i) Preparation of a Plasmid Having the gltA Gene, ppc Gene, and gdhA Gene from *Escherichia coli*

Figure 2:
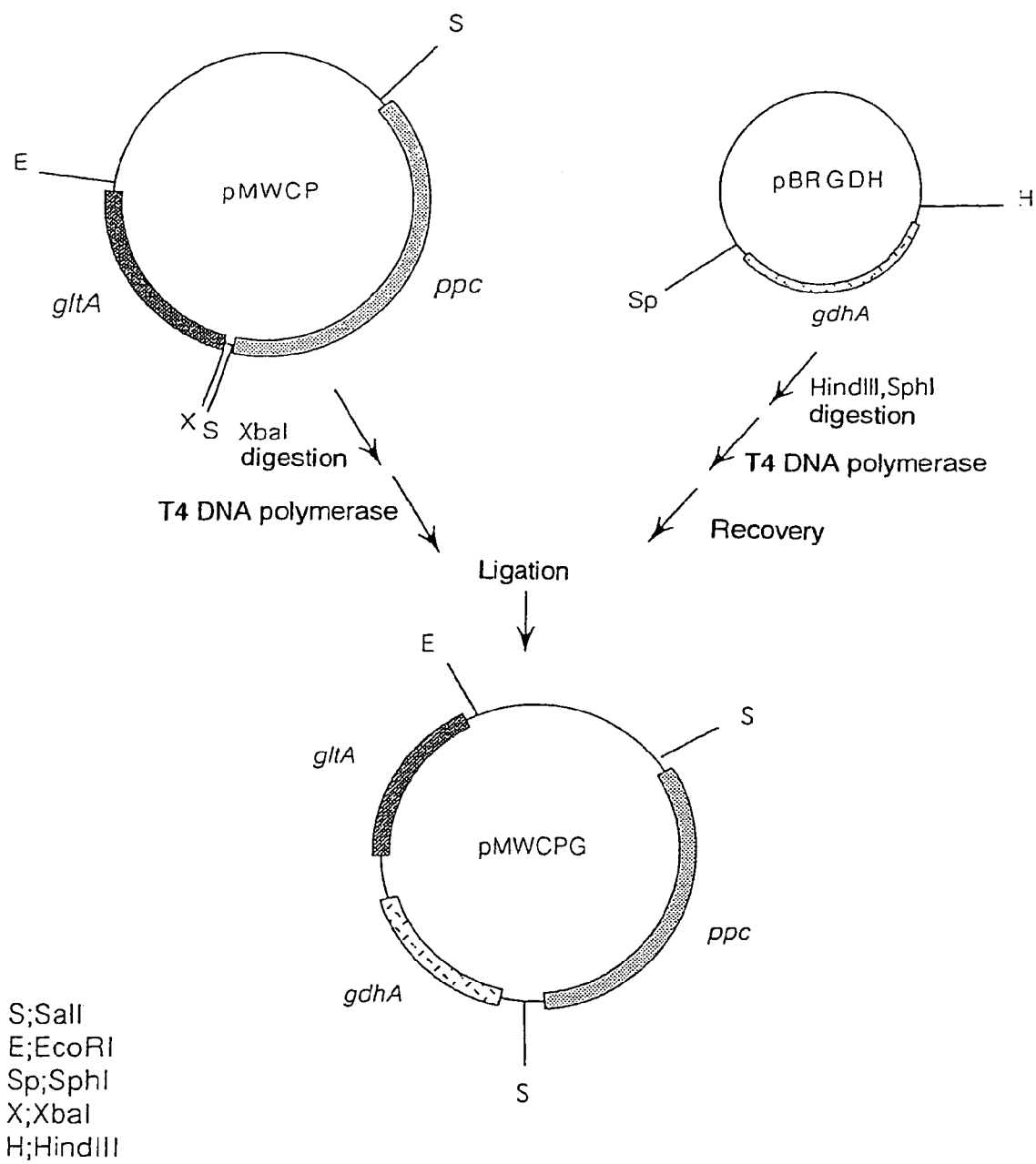
FIG. 2 shows construction of the plasmid pMWCPG which contains genes gltA, ppc, and gdhA.
Figure 3:
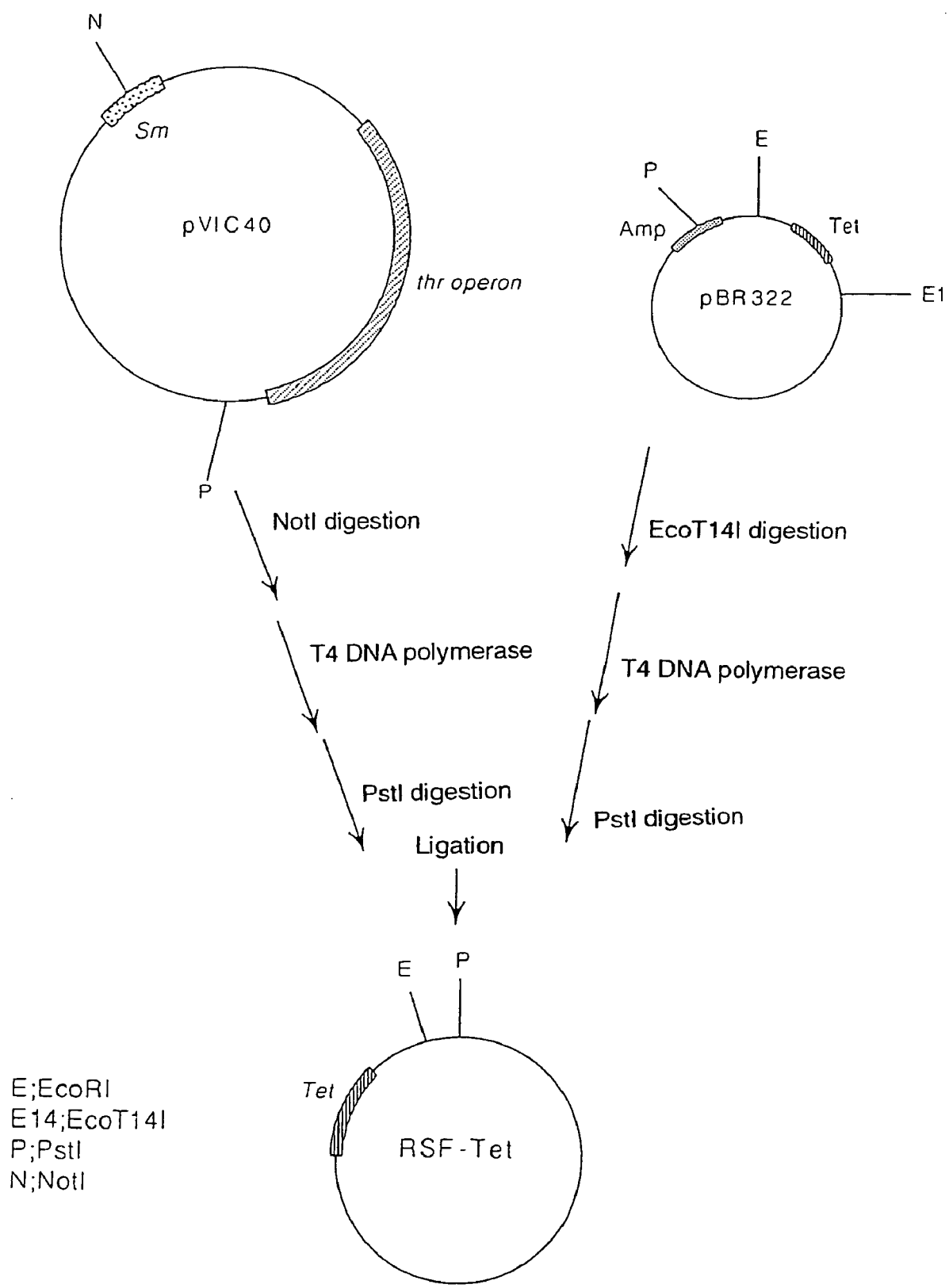
FIG. 3 shows construction of the plasmid RSF-Tet which contains the replication origin of the wide host range plasmid RSF1010 and the tetracycline resistance gene.

The procedures for preparing a plasmid having the gltA gene, the ppc gene, and the gdhA gene will be explained by referring to FIGS. 2 and 3.

A plasmid having the gdhA gene from *Escherichia coli*, pBRGDH (Japanese Patent Application Laid-open No. 7-203980), was digested with HindIII and SphI, then both ends were blunt-ended by treatment with T4 DNA polymerase, and then the DNA fragment having the gdhA gene was purified and recovered. Separately, a plasmid having the gltA gene and ppc gene from *Escherichia coli*, pMWCP (WO97/08294), was digested with XbaI, and then both ends were blunt-ended by treatment with T4 DNA polymerase. This was mixed with the above-purified DNA fragment having the gdhA gene and ligated using T4 ligase to obtain the plasmid pMWCPG, which is pMWCP with the gdhA gene (FIG. 2).

Concurrently, the plasmid pVIC40 (Japanese Patent Application Laid-open No. 8-047397) having the replication origin of the wide-host-range plasmid RSF1010 was digested with NotI, treated with T4 DNA polymerase, and digested with PstI. pBR322 was digested with EcoT14I, treated with T4 DNA polymerase, and digested with PstI. Both products were mixed and ligated using T4 ligase to obtain the plasmid RSF-Tet having the replication origin of RSF1010 and the tetracycline resistance gene (FIG. 3).

Figure 4:
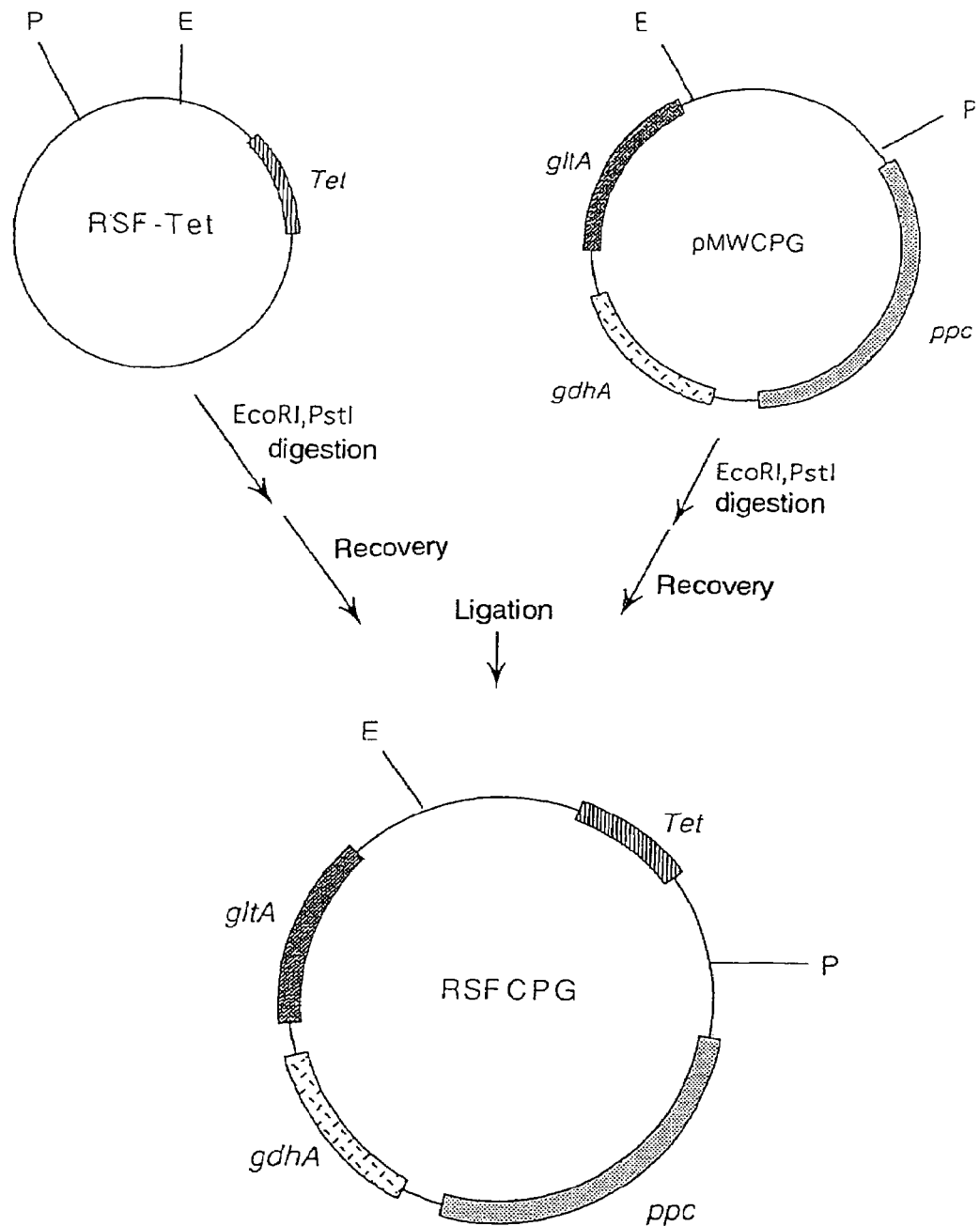
FIG. 4 shows construction of a plasmid RSFCPG containing the replication origin of the wide host range plasmid RSF1010, tetracycline resistance gene, gltA gene, ppc gene, and gdhA gene.

Subsequently, pMWCPG was digested with EcoRI and PstI, and a DNA fragment having the gltA gene, the ppc gene, and the gdhA gene was purified and recovered. RSF-Tet was similarly digested with EcoRI and PstI, and a DNA fragment having the replication origin of RSF110 was purified and recovered. Both products were mixed and ligated using T4 ligase to obtain a plasmid RSFCPG, which corresponds to RSF-Tet containing the gltA gene, the ppc gene, and the gdhA gene (FIG. 4). It was confirmed that the obtained plasmid RSFCPG expressed the gltA gene, the ppc gene, and the gdhA gene based on the supplementation of the auxotrophy of the gltA gene-, ppc gene- or gdhA gene-deficient strain derived from *Escherichia coli* and measuring each enzyme activity.

(ii) Preparation of a Plasmid Having gltA Gene Derived from *Brevibacterium lactofermentum*

Figure 5:
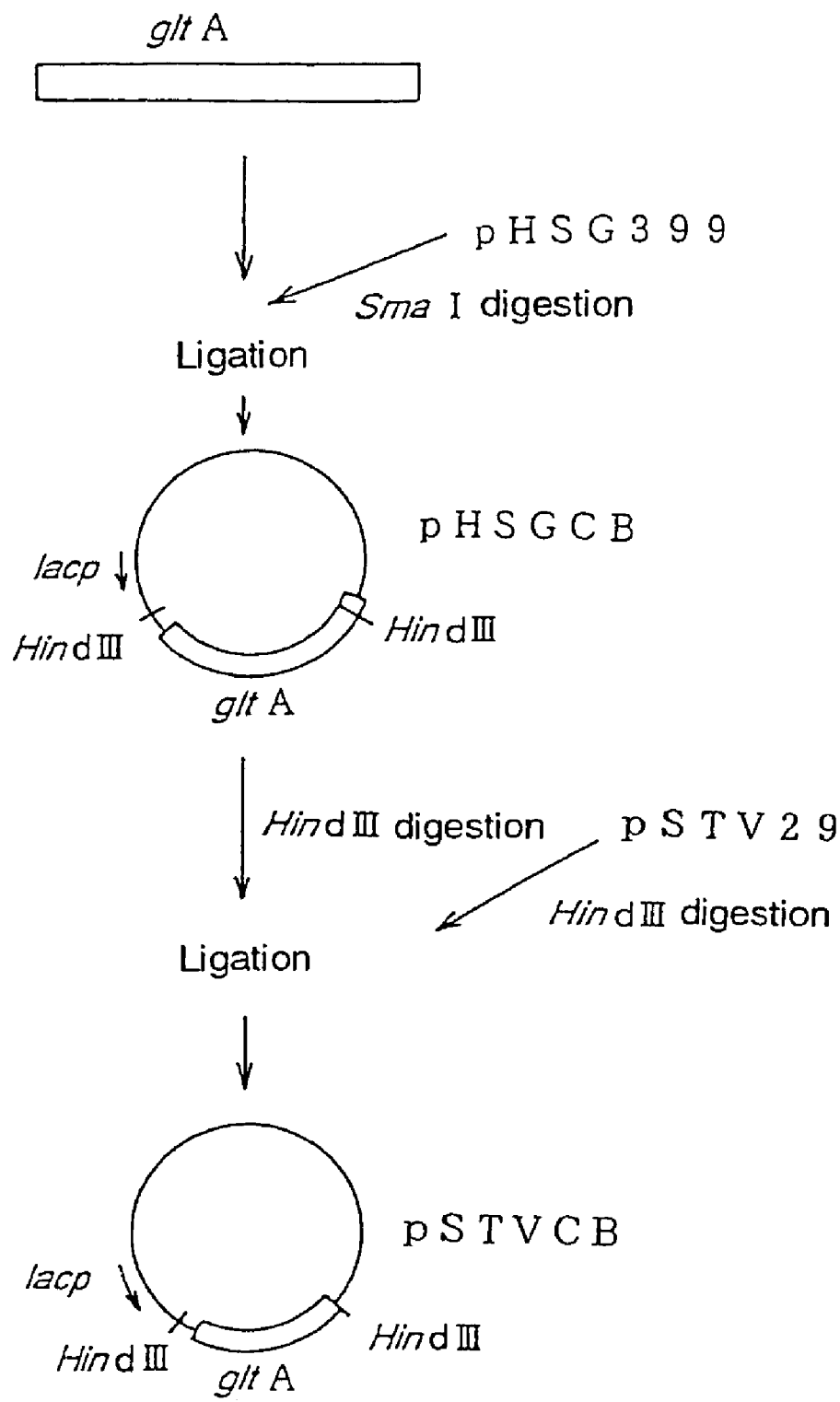
FIG. 5 shows construction of the plasmid pSTVCB which contains the gltA gene.

A plasmid having the gltA gene from *Brevibacterium lactofermentum* was constructed as follows. PCR was performed using the primer DNAs having the nucleotide sequences shown in SEQ ID NOS: 6 and 7, which were prepared based on the nucleotide sequence of the *Corynebacterium glutamicum* gltA gene (Microbiology, 140, pp. 1817-1828 (1994)), and the chromosomal DNA of *Brevibacterium lactofermentum* ATCC13869 as a template to obtain a gltA gene fragment of about 3 kb. This fragment was inserted into plasmid pHSG399 (purchased from Takara Shuzo Co., Ltd.) which had been digested with SmaI, to obtain plasmid pHSGCB (FIG. 5). Subsequently, pHSGCB was digested with HindIII, and the excised gltA gene fragment of about 3 kb was inserted into plasmid pSTV29 (purchased from Takara Shuzo Co., Ltd.) which had been digested with HindIII to obtain plasmid pSTVCB (FIG. 5). It was confirmed that the plasmid pSTVCB expressed the gltA gene by measuring the enzyme activity in the *Pantoea ananatis* AJ13355 strain.

(iii) Introduction of RSFCPG and pSTVCB into the SC17sucA Strain

The *Pantoea ananatis* SC17sucA strain was transformed with RSFCPG by electroporation to obtain a transformant SC17sucA/RSFCPG strain which was resistant to tetracycline. Furthermore, the SC17sucA/RSFCPG strain was transformed with pSTVCB by electroporation to obtain a transformant SC17sucA/RSFCPG+pSTVCB strain which was resistant to chloramphenicol.

<5> Acquisition of a Strain with Improved Resistance to L-Glutamic Acid in a Low pH Environment A strain with improved resistance to high concentrations of L-glutamic acid in a low pH environment (hereafter, also referred to as "strain with high-concentration Glu-resistance at low pH") was isolated from the *Pantoea ananatis* SC17sucA/RSFCPG+pSTVCB strain.

The SC17sucA/RSFCPG+pSTVCB strain was cultured overnight at 30° C. in LBG medium (10 g/L of trypton, 5 g/L of yeast extract, 10 g/L of NaCl, 5 g/L of glucose), and the cells washed with saline were appropriately diluted and plated on an M9-E medium plate (4 g/L of glucose, 17 g/L of $Na_2HPO_4.12H_2O$, 3 g/L of $KH_2PO_4$, 0.5 g/L of NaCl, 1 g/L of $NH_4Cl$, 10 mM of $MgSO_4$, 10 µM of $CaCl_2$, 50 mg/L of L-lysine, 50 mg/L of L-methionine, 50 mg/L of DL-diaminopimelic acid, 25 mg/L of tetracycline, 25 mg/L of chloramphenicol, 30 g/L of L-glutamic acid, adjusted to pH 4.5 with aqueous ammonia). A colony which emerged after culture at 32° C. for 2 days was obtained as a strain with high-concentration Glu-resistance at low pH.

For the obtained strain, the growth level in M9-E liquid medium was measured and L-glutamic acid-producing ability was tested in a 50-ml volume large test tube containing 5 ml of a L-glutamic acid production test medium (40 g/L of glucose, 20 g/L of ammonium sulfate, 0.5 g/L of magnesium sulfate heptahydrate, 2 g/L of potassium dihydrogenphosphate, 0.5 g/L of sodium chloride, 0.25 g/L of calcium chloride dihydrate, 0.02 g/L of ferrous sulfate heptahydrate, 0.02 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, 2 g/L of yeast extract, 200 mg/L of L-lysine hydrochloride, 200 mg/L of L-methionine, 200 mg/L of DL-α,ε-diaminopimelic acid, 25 mg/L of tetracycline hydrochloride, and 25 mg/L of chloramphenicol). A strain that exhibited the best growth and the same L-glutamic acid-producing ability as that of its parent strain, the SC17/RSFCPG+pSTVCB strain, was designated *Pantoea ananatis* AJ13601. The AJ13601 strain was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Aug. 18, 1999 and received an accession number of FERM P-17516. It was then converted to an international deposit under the provisions of Budapest Treaty on Jul. 6, 2000 and received an accession number of FERM BP-7207.

Example 1

Studies on the Effect of L-Lysine on Maximum Saturated Concentration of L-Glutamic Acid Cells of the *Pantoea ananatis* AJ13601 strain cultured at 30° C. for 14 hours in the LBG agar medium (10 g/L of trypton, 5 g/L of yeast extract, 10 g/L of NaCl, 15 g/L of agar) containing 25 mg/L of tetracycline hydrochloride and 25 mg/L of chloramphenicol were scraped from one plate and inoculated into 300 ml of seed culture medium having the following composition and contained in a 1 L-volume jar fermenter, and seed culture was performed at 34° C. and pH 6.0.

Composition of Seed Culture Medium:

| | |
|---|---|
| Sucrose | 50 g/L |
| $MgSO_4·7H_2O$ | 0.4 g/L |
| $KH_2PO_4$ | 2.0 g/L |
| Yeast extract | 4.0 g/L |
| $FeSO_4·7H_2O$ | 0.01 g/L |
| $MnSO_4·5H_2O$ | 0.01 g/L |
| L-Lysine hydrochloride | 0.4 g/L |
| DL-Methionine | 0.4 g/L |

-continued

| | |
|---|---|
| ε-Diaminopimelic acid | 0.4 g/L |
| Tetracycline hydrochloride | 25 mg/L |
| Chloramphenicol | 25 mg/L |

The pH was adjusted to 6.0 by adding ammonia gas during the culture. The seed culture was finished by observing depletion of the saccharide in the medium as an index, and the seed culture medium of 20% volume of the main culture medium was inoculated into 300 ml of the main culture medium contained in a 1 L-volume jar fermenter to perform the main culture under the conditions of 34° C. and pH 4.5. The composition of the main culture medium is shown below.

Composition of Main Culture Medium:

| | |
|---|---|
| Glucose | 50 g/L |
| $(NH_4)_2SO_4$ | 5.0 g/L |
| $MgSO_4 \cdot 7H_2O$ | 0.4 g/L |
| $KH_2PO_4$ | 6.0 g/L |
| NaCl | 1.5 g/L |
| $FeSO_4 \cdot 7H_2O$ | 0.01 g/L |
| $MnSO_4 \cdot 5H_2O$ | 0.01 g/L |
| L-Lysine hydrochloride | 0.8 g/L |
| DL-Methionine | 0.6 g/L |
| DL-α,ε-Diaminopimelic acid | 0.6 g/L |
| Tetracycline hydrochloride | 25 mg/L |
| Chloramphenicol | 25 mg/L |
| Calcium chloride dihydrate | 0.75 g/L |

The pH was adjusted to 4.5 by adding ammonia gas during the culture. After the saccharide in the medium was consumed and depleted, 700 g/L of glucose aqueous solution was continuously added (6 ml/hr).

Figure 6:
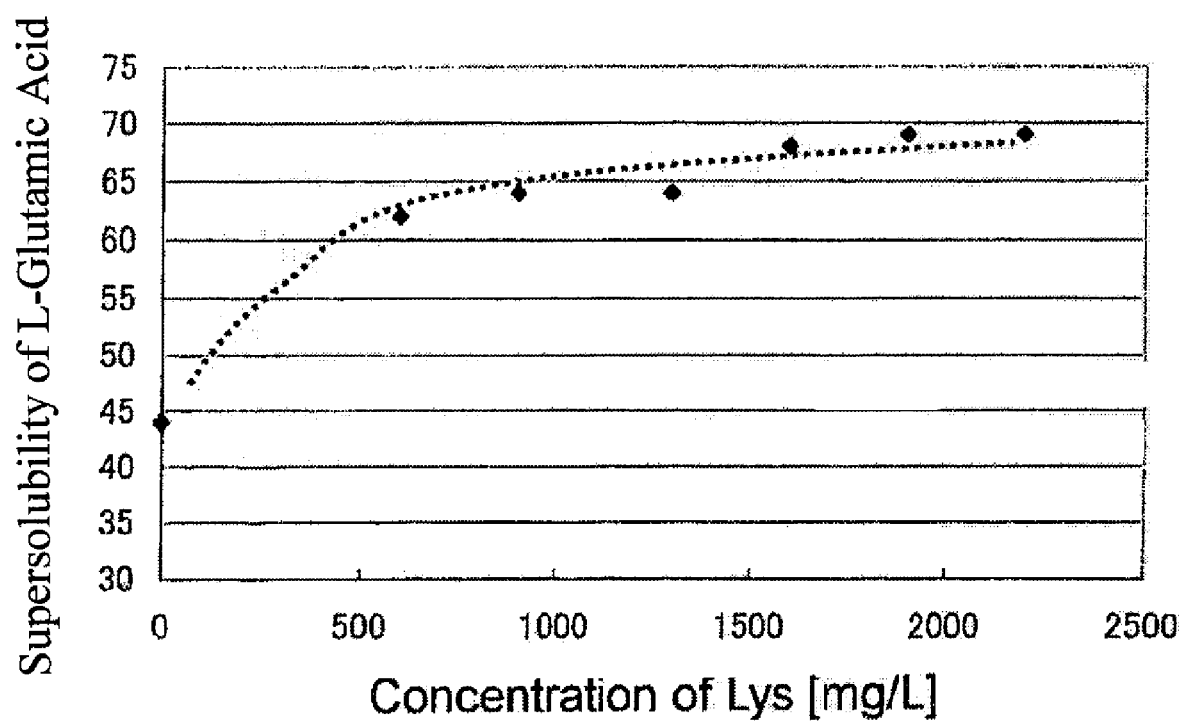
FIG. 6 is a graph showing the relationship between the supersolubility of L-glutamic acid and the concentration of L-lysine.

Once the L-glutamic acid concentration in the medium exceeds 40 g/L, 0 to 0.9 g L-lysine hydrochloride was added per 300 ml of the culture medium. Then, the L-glutamic acid concentration in the supernatant of the culture medium was measured over time. The liquid supernatant of the culture medium was obtained by centrifuging the culture medium at 10000×G for 1 minute. The polymorphism of crystals which precipitated in the culture medium was determined by microscopic observation. The L-glutamic acid concentration in the culture medium increases with time, and the L-glutamic acid concentration in the supernatant liquid decreases as the crystals are precipitated. Therefore, the maximum concentration of L-glutamic acid in the supernatant was defined as the precipitation concentration thereof. The results are shown in FIG. 6.

In a culture system at pH 4.5, 44 g/L of L-glutamic acid β-form crystals precipitates in an L-lysine-free culture medium. The solubility of L-glutamic acid at pH 4.5 is 40 g/L. Therefore, the addition of seed crystals should be performed at concentrations ranging from 40 g/L to 44 g/L. This range correlates to 50 minutes when the production rate of L-glutamic acid in the culture is 5 g/L/h, and therefore extremely precise control is required to avoid an analytical error. In contrast, when 600 mg/L of L-lysine is present in the system, the concentration at which precipitation of β-form crystals occurs increases to 62 g/L and the permissible range of seed-crystal addition extends to 40 g/L to 62 g/L. This correlates to 4 hours of the production rate of L-glutamic acid is 5 g/L/h, and therefore the control becomes extremely easy. Furthermore, the super solubility of L-glutamic acid increases as the concentration of L-lysine increases (FIG. 6).

The above phenomenon is considered to occur as a result of inhibiting crystal growth by adsorption of L-lysine on the crystal plane of α-form crystals of L-glutamic acid. Thus, significant super saturation is required to attain the crystal growth (including the generation of nucleus) sufficient to merge an increase in glutamic-acid concentration with culture. Therefore, it is presumed that super saturation increases as the concentration of L-lysine increases.

When the concentration of added L-lysine exceeds 900 mg/L, α-form crystals form naturally even without the addition of seed crystals. This is because L-lysine may inhibit crystal growth by its strong adsorption to the surface of β-form crystals rather than α-form crystals at pH 4.5. Accordingly, it is presumed that the crystal growth of β-form crystals is suppressed to allow crystallization of the α-form crystals due to the presence of L-lysine at a certain concentration or more.

(2) Control of the Crystal Form of L-Glutamic Acid Crystals with L-Lysine

Figure 7:
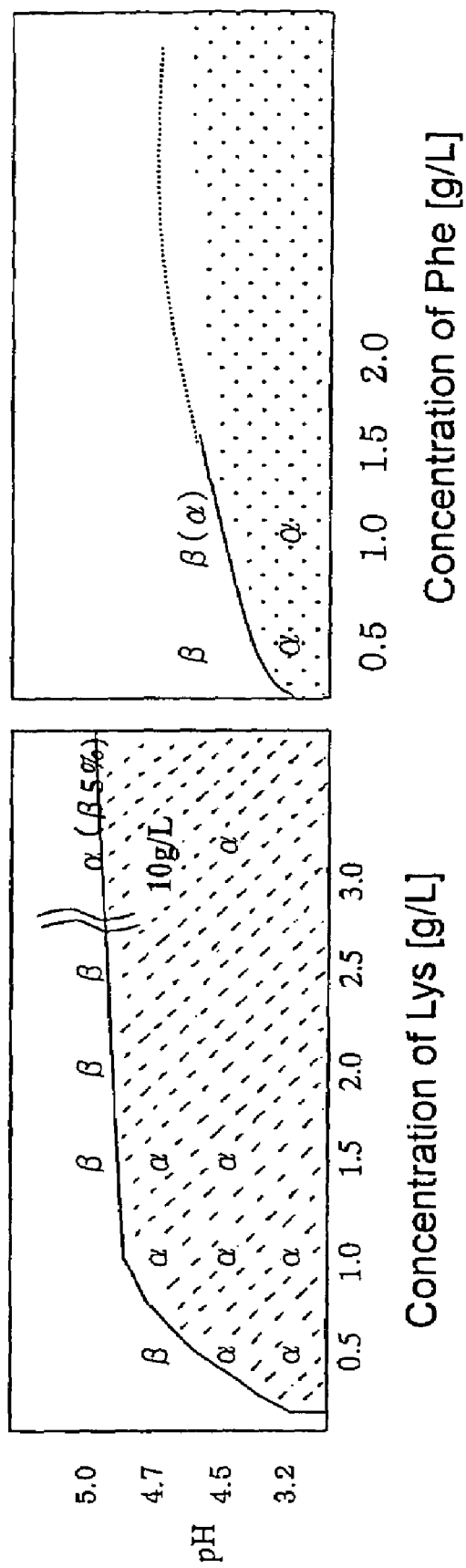
FIG. 7 is a graph showing the relationship between the concentration of added L-lysine or L-phenylalanine and the pH of the solution. The graph indicates that at pH 4.5, the crystal form precipitated by the addition of L-lysine could be controlled to the α-form.

Next, L-glutamic acid was dissolved in water so as to obtain super saturation (Css/Cs[-]) of 2, and then the pH and the L-lysine concentration of the medium were changed to investigate the crystal form of L-glutamic acid crystals which precipitate in a cooling-crystallization system (34° C.). The pH was adjusted by adding ammonia water. In addition, instead of L-lysine, L-phenylalanine was added and the same experiment was performed. The results are shown in FIG. 7. Furthermore, the solubility and the glutamic-acid concentration at each pH are listed in Table 1.

As shown in FIG. 7, at pH 4.5, the crystal form precipitated by the addition of L-lysine could be controlled to the α-form. On the other hand, L-phenylalanine showed the same effect at pH 3.2, but such an effect could not be observed at pH 4.5 or more. The difference between the two may be due to the fact that the amino acids induce different dissociation states at each pH.

TABLE 1

| pH | Solubility (g/100 g $H_2O$) | L-glutamic acid concentration(g/100 g $H_2O$) |
|---|---|---|
| 3.2 | 1.2 | 2.4 |
| 4.5 | 4 | 8 |
| 4.7 | 6 | 12 |
| 5 | 10 | 20 |

INDUSTRIAL APPLICABILITY

In the method for producing L-glutamic acid by fermentation while precipitating L-glutamic acid in a medium, α-form crystals of L-glutamic acid can be precipitated without the addition of seed crystals by adding L-lysine to the medium.

Also, it is easy to control the timing of the addition of seed crystals adding L-lysine to the medium.

While the invention has been described in detail with reference to preferred embodiments thereof, it will be apparent to one skilled in the art that various changes can be made, and equivalents employed, without departing from the scope of the invention. Each of the aforementioned documents, including the foreign priority document JP2003-128722, is incorporated by reference herein in its entirety.

What is claimed is:

1. A method for producing L-glutamic acid by fermentation comprising:

a) culturing a microorganism in a liquid medium within a pH range which is controlled so that L-glutamic acid precipitates, wherein said medium contains a carbon source able to be metabolized by said microorganism when the medium is at least saturated with L-glutamic acid wherein said microorganism is an L-glutamic acid-producing microorganism selected for resistance to L-glutamic acid;

b) adding L-lysine to the medium once the culture solution is saturated or over-saturated with L-glutamic acid, and when the L-glutamic acid concentration is lower than the concentration at which natural crystallization of L-glutamic acid occurs; and c) collecting α-form crystals of L-glutamic acid.

2. The method according to claim 1, wherein the microorganism belongs to the genus *Pantoea*.

3. The method according to claim 2, wherein the microorganism is *Pantoea ananatis*.

4. The method according to claim 1, wherein L-lysine is added to a concentration of 900 mg/L or more.

5. The method according to claim 1, wherein the pH of the medium at or after addition of L-lysine is 3.0 to 5.0.

6. The method according to claim 1, wherein α-form crystals are added to the medium before natural crystallization of L-glutamic acid occurs.

* * * * *